US011357409B2

(12) United States Patent
Hirohata et al.

(10) Patent No.: US 11,357,409 B2
(45) Date of Patent: Jun. 14, 2022

(54) BLOOD VESSEL ANALYSIS APPARATUS, MEDICAL IMAGE DIAGNOSIS APPARATUS, AND BLOOD VESSEL ANALYSIS METHOD

(71) Applicant: Kabushiki Kaisha Toshiba, Minato-ku (JP)

(72) Inventors: Kenji Hirohata, Tokyo (JP); Junichiro Ooga, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 1204 days.

(21) Appl. No.: 14/716,433

(22) Filed: May 19, 2015

(65) Prior Publication Data

US 2015/0245776 A1 Sep. 3, 2015

Related U.S. Application Data

(63) Continuation of application No. PCT/JP2013/080502, filed on Nov. 12, 2013.

(30) Foreign Application Priority Data

Nov. 19, 2012 (JP) .............................. JP2012-253619

(51) Int. Cl.
*A61B 5/026* (2006.01)
*A61B 5/02* (2006.01)
(Continued)

(52) U.S. Cl.
CPC .......... *A61B 5/02007* (2013.01); *A61B 5/026* (2013.01); *A61B 5/055* (2013.01);
(Continued)

(58) Field of Classification Search
CPC ... A61B 5/02007; A61B 6/504; A61B 6/5217; A61B 5/026; A61B 5/055; A61B 6/037;
(Continued)

(56) References Cited

U.S. PATENT DOCUMENTS 7,653,510 B2    1/2010    Hirohata et al.
8,157,742 B2    4/2012    Taylor
(Continued)

FOREIGN PATENT DOCUMENTS

CN    101542530 A    9/2009
CN    101686825 A    3/2010
(Continued)

OTHER PUBLICATIONS

International Search Report dated Feb. 10, 2014 for PCT/JP2013/080502 filed Nov. 12, 2013 with English Translation.
(Continued)

*Primary Examiner* — Navin Natnithithadha
(74) *Attorney, Agent, or Firm* — Oblon, McClelland, Maier & Neustadt, L.L.P.

(57) ABSTRACT

A time-series morphology index and a time-series shape deformation index of the analysis target region on a time-series medical image are calculated by image processing. A dynamical model of a structural fluid analysis of the analysis target region is temporarily structured, based on the time-series morphology index, the time-series shape deformation index, and the time-series medical image. A latent variable of the identification region is identified so that at least one of a prediction value of a blood vessel morphology index and a blood flow volume index based on the temporarily structured dynamical model match with at least one of an observation value of the blood vessel morphology index and the blood flow volume index measured.

15 Claims, 16 Drawing Sheets

(51) Int. Cl.
*A61B 5/055* (2006.01)
*A61B 6/03* (2006.01)
*A61B 8/06* (2006.01)
*G06T 7/00* (2017.01)
*A61B 6/00* (2006.01)

(52) U.S. Cl.
CPC .............. *A61B 6/032* (2013.01); *A61B 6/037* (2013.01); *A61B 6/504* (2013.01); *A61B 6/5217* (2013.01); *A61B 8/06* (2013.01); *G06T 7/0016* (2013.01); *A61B 6/481* (2013.01); *G06T 2207/10072* (2013.01); *G06T 2207/10136* (2013.01); *G06T 2207/30104* (2013.01)

(58) Field of Classification Search
CPC ........... A61B 8/06; A61B 6/032; A61B 6/481; G06T 7/0016; G06T 2207/10136; G06T 2207/30104; G06T 2207/10072; G16H 50/30
See application file for complete search history.

(56) References Cited

U.S. PATENT DOCUMENTS

| | | | |
|---|---|---|---|
| 8,249,815 B2 | 8/2012 | Taylor | |
| 8,311,747 B2 | 11/2012 | Taylor | |
| 8,311,748 B2 | 11/2012 | Taylor et al. | |
| 8,311,750 B2 | 11/2012 | Taylor | |
| 8,315,812 B2 | 11/2012 | Taylor | |
| 8,315,813 B2 | 11/2012 | Taylor et al. | |
| 8,315,814 B2 | 11/2012 | Taylor et al. | |
| 8,321,150 B2 | 11/2012 | Taylor | |
| 9,928,593 B2* | 3/2018 | Ooga | A61B 6/03 |
| 2003/0233039 A1 | 12/2003 | Shao et al. | |
| 2006/0069318 A1 | 3/2006 | Keaveny et al. | |
| 2008/0294038 A1 | 11/2008 | Weese et al. | |
| 2010/0054559 A1 | 3/2010 | Narayanan | |
| 2010/0183206 A1 | 7/2010 | Carlsen et al. | |
| 2011/0103665 A1 | 5/2011 | Gulsun et al. | |
| 2012/0041318 A1* | 2/2012 | Taylor | A61B 6/503 600/504 |
| 2013/0158970 A1 | 6/2013 | Hof et al. | |

FOREIGN PATENT DOCUMENTS

| | | |
|---|---|---|
| CN | 104736061 A | 6/2015 |
| JP | 2008-514368 A | 5/2008 |
| JP | 2008-241432 A | 10/2008 |
| JP | 2009-518097 A | 5/2009 |
| WO | WO 2012/021307 A2 | 2/2012 |
| WO | WO 2012/028190 A1 | 3/2012 |

OTHER PUBLICATIONS

Written Opinion dated Feb. 10, 2014 for PCT/JP2013/080502 filed Nov. 12, 2013.
Kadooka, Yoshimasa, *Journal of the ITU Association of Japan*, vol. 41, No. 6 (Jun. 2011), pp. 41-44.
Combined Chinese Office Action and Search Report dated Dec. 20, 2016 in Patent Application No. 201380054742.6 (with English Translation of Categories of Cited Documents).
Office Action dated Aug. 8, 2017 in Japanese Patent Application No. 2016-201764.

* cited by examiner

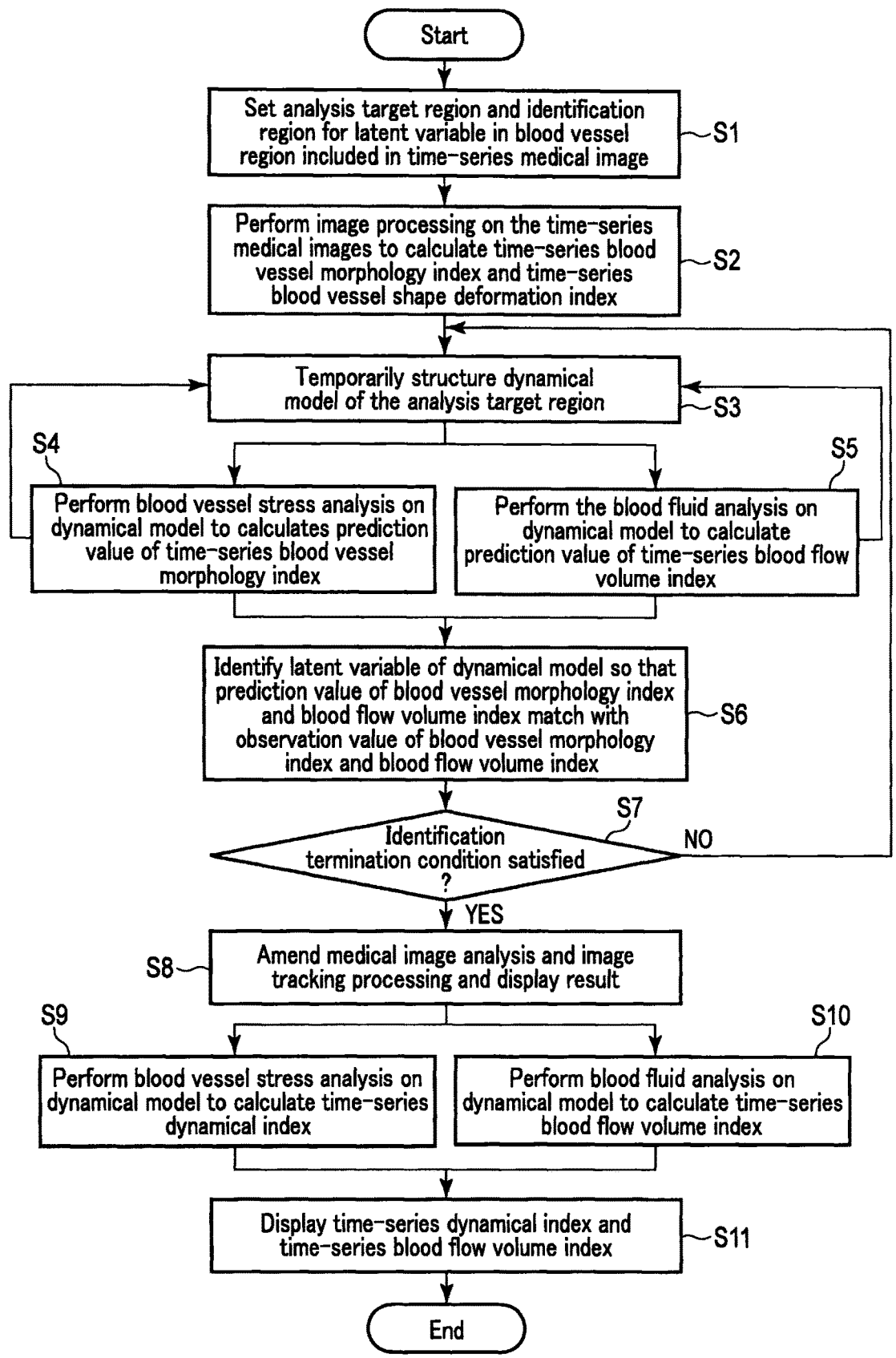
F I G. 3

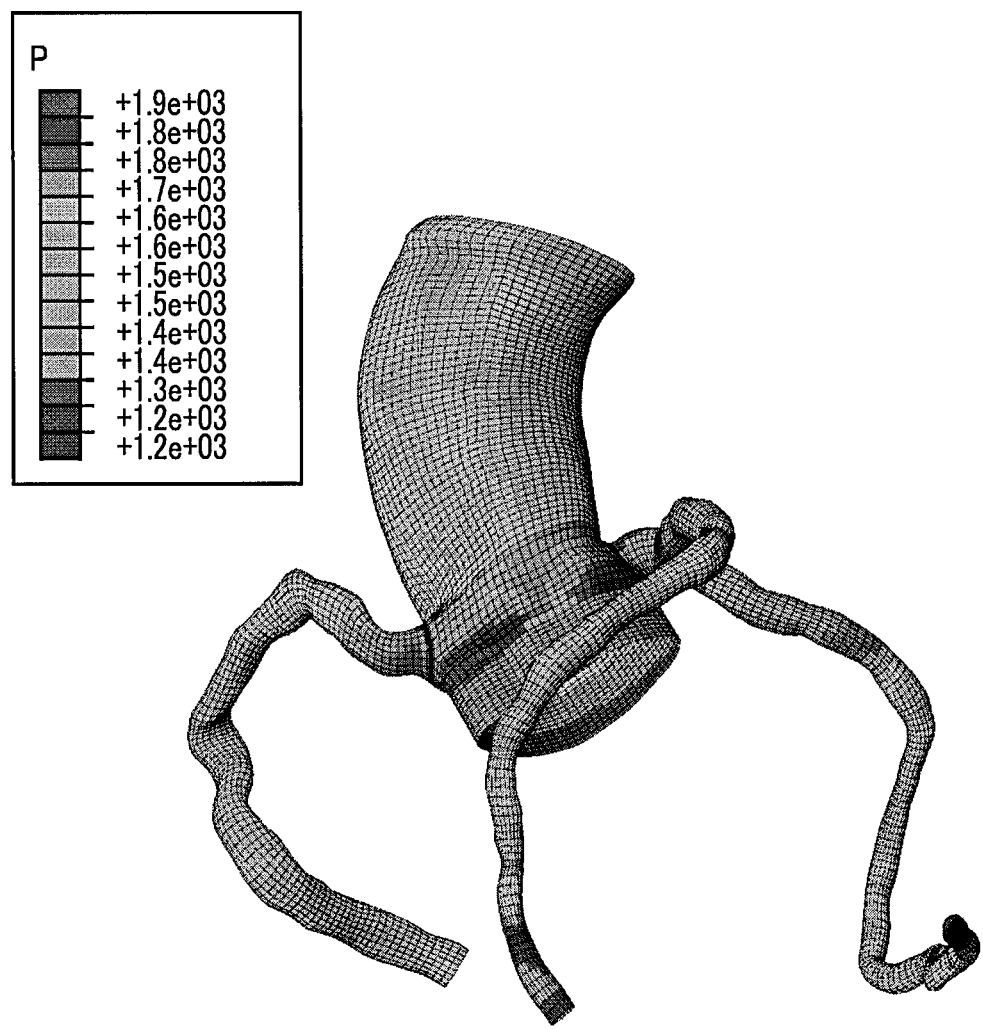
F I G. 15

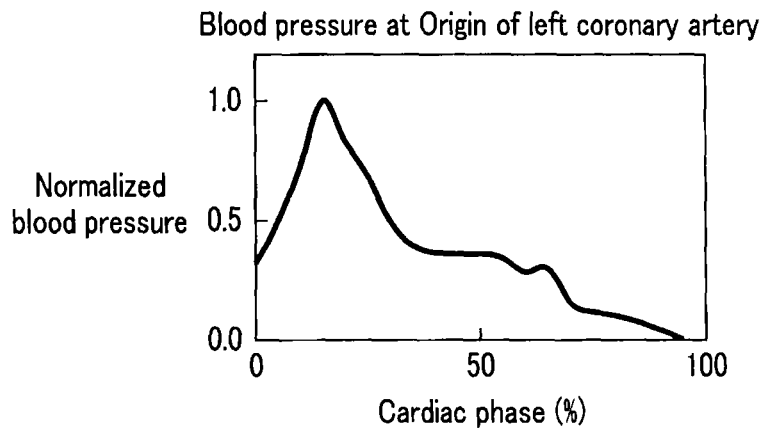
F I G. 17
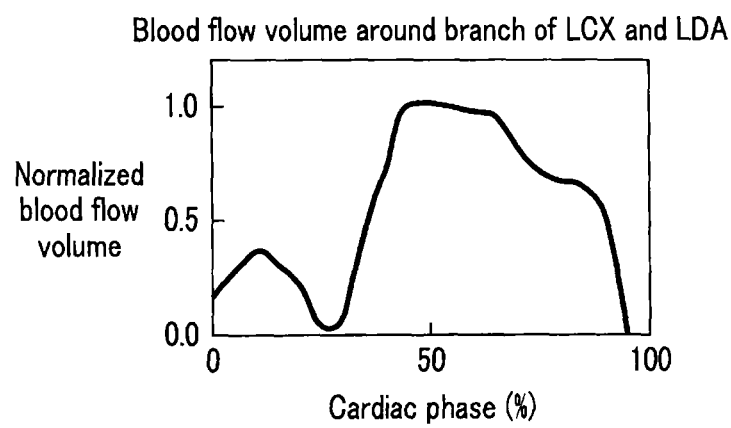
F I G. 18
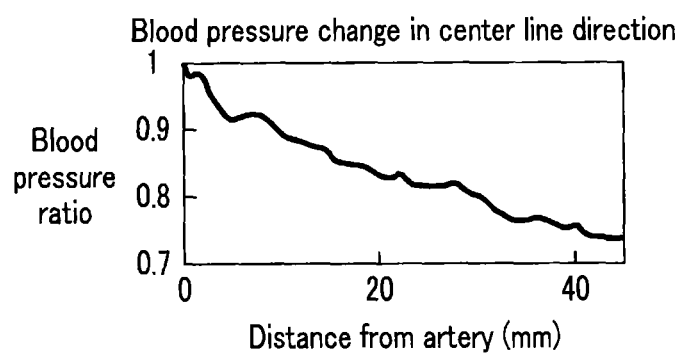
F I G. 19

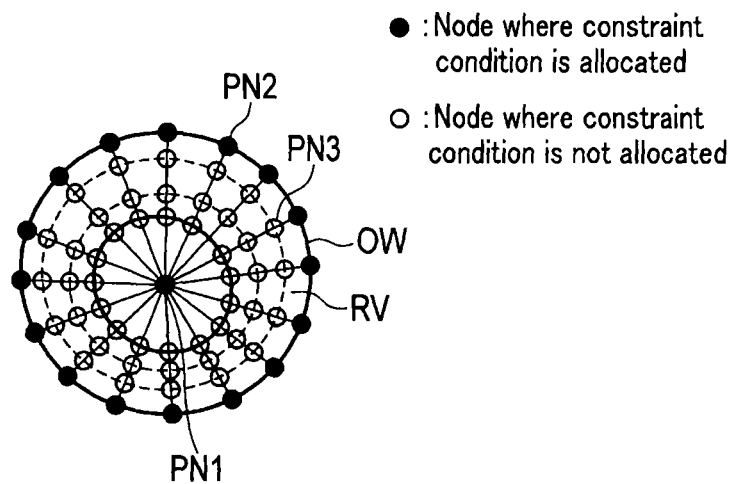

● : Node where constraint condition is allocated

○ : Node where constraint condition is not allocated

Case where constraint is given only to external surface with forcible displacement history
Latent variable
(boundary condition, material model, and load condition are identified)

FIG. 20A

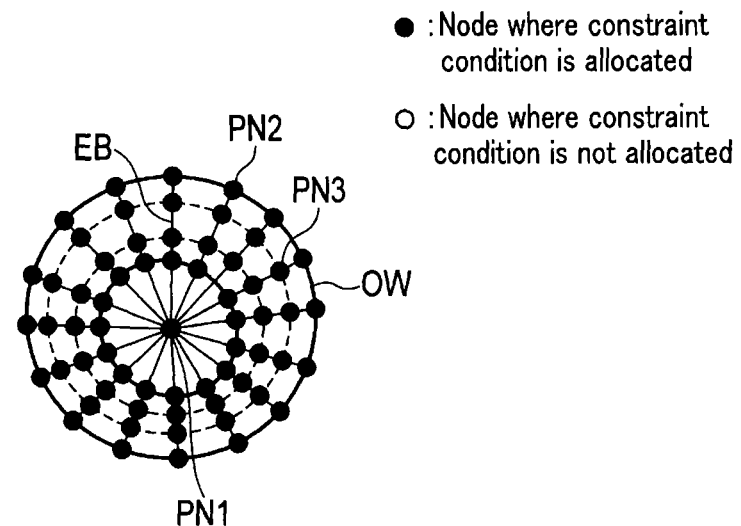

● : Node where constraint condition is allocated

○ : Node where constraint condition is not allocated

Case where constraint is given also to lumen side with forcible displacement history
Latent variable
(boundary condition, material model, and load condition are identified)

FIG. 20B

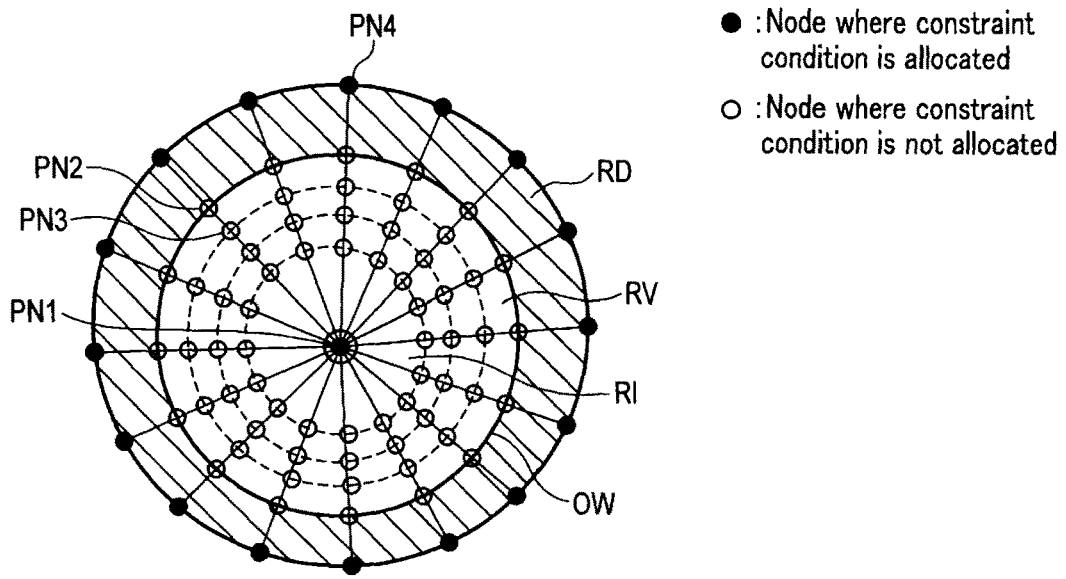

Case where constraint is given by giving forcible displacement history to nodes of dummy element surface around blood vessel wall (latent variable is identified by referring to not only lumen shape index but also blood vessel wall shape index (case where boundary condition, material model, and load condition are identified))

F I G. 21

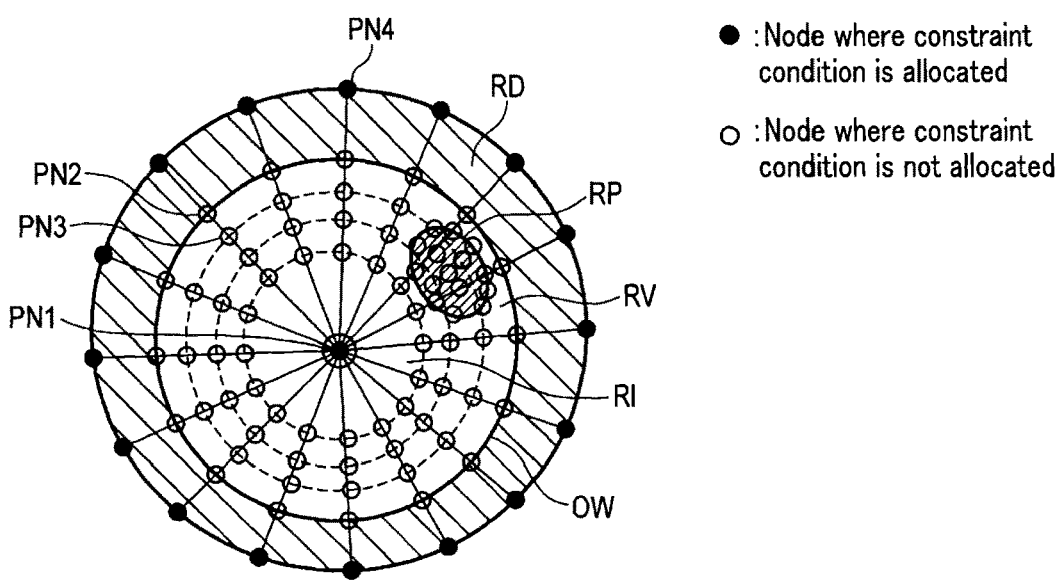

Latent variables of plaque and blood vessel wall are respectively identified by referring to not only lumen shape index but also blood vessel wall shape index and plaque shape index (case where boundary condition, material model, and load condition are identified))

F I G. 22

BLOOD VESSEL ANALYSIS APPARATUS, MEDICAL IMAGE DIAGNOSIS APPARATUS, AND BLOOD VESSEL ANALYSIS METHOD

CROSS-REFERENCE TO RELATED APPLICATIONS

This application is a Continuation Application of PCT Application No. PCT/JP2013/080502, filed Nov. 12, 2013 and the prior Japanese Patent Application 2012-253619, filed Nov. 19, 2012 the entire contents of all of which are incorporated herein by reference.

FIELD

Embodiment described herein relate generally to a blood vessel analysis apparatus, a medical image diagnosis apparatus, and a blood vessel analysis method.

BACKGROUND

It is desired to develop a noninvasive or minimally invasive technique for preventing and diagnosing stenosis of a coronary artery causing heart disease which is one of three major diseases, cerebral aneurysm, or stenosis caused by a plaque of a carotid artery which may be a premonition thereof.

Stenosis of a coronary artery is a serious pathologic change that may lead to ischemic heart disease. A diagnosis of stenosis of a coronary artery is mainly Coronary Angiography (CAG) using a catheter. A diagnosis index of an organic pathologic change of a coronary artery includes Fractional Flow Reserve (FFR). The FFR is defined as a ratio of the maximum coronary blood flow where stenosis exists with respect to the maximum coronary blood flow where stenosis does not exist. The FFR is substantially the same as the ratio of a stenosis distal portion coronary internal pressure with respect to a stenosis proximal portion coronary internal pressure. A pressure sensor provided at a catheter distal end is measured. More specifically, a catheter operation is required to measure the FFR.

When the analysis of stenosis of the coronary artery can be performed with a heart CT, this is minimally invasive, and can reduce the burden imposed on the patient and save the medical cost as compared with the measurement of the FFR with the catheter operation. However, in the heart CT, only the index based on the size of a stenosed region or a plaque region included in a CT image can be measured in a minimally invasive manner. If a pressure difference and the like before and after the stenosis can be measured based on the CT image by structural fluid analysis, the effect exerted by the stenosis (or the plaque) is expected to be quantified.

Ultra-fast CT, cine angiography grams, ultrasonic method, nuclear medicine imaging including SPECT (single photon emission tomography) and PET (positron emission tomography), MRI (magnetic resonance image method), and the like have been developed and introduced in terms of clinical aspect as a dynamic evaluation of coronary circulation, and are useful for evaluation of diagnosis and treatment method.

However, it is difficult for a medical image diagnosis apparatus to accurately recognize coronary microvessels. Even if a blood vessel shape is clear, a medical image may include noises, and the threshold value setting at the boundary of a living tissue may be ambiguous. As described above, a blood vessel shape obtained by the medical image diagnosis apparatus involves uncertainty.

When a medical image diagnosis apparatus is utilized in a clinical application, analysis is often performed on the target of only a thick region of coronary artery from the origin of the pulmonary artery at the upstream of the coronary microvessels. Since the bloodstream of the coronary artery is also greatly affected by the tonic (tonus) of the coronary microvessels, it is the problem to appropriately set boundary conditions of fluid analysis such as the amount of flow or pressure at the exit of the coronary artery of the thick region or the rate of change thereof. The bloodstream of the coronary artery receives mechanical factors of pulsation of the heart (overall movement caused by pulsation, and forcible displacement or external force due to local extension, torsion, and shear deformation). With the fluid analysis alone, the effect of the mechanical factors such as pulsation of the heart cannot be taken into consideration, and therefore, the amount of flow distribution of the bloodstream and the internal pressure distribution cannot be accurately measured. On the other hand, a structure-fluid interaction analysis is also carried out on the heart and the blood vessel system recognized in an image in view of the effects of the mechanical factors. However, even when the structure-fluid interaction analysis is performed, it is often difficult to correctly set the material model of the blood vessel and the plaque and the boundary condition at the entrance and the exit of the blood vessel in the fluid analysis of the blood (including contrast medium). When there is a microvessel that is not drawn in the image, the effect of the microvessel given to the bloodstream cannot be taken into consideration. For this reason, the analysis result of the structure-fluid interaction analysis may not be reproducing actual bloodstream and blood vessel deformation. In a case where the boundary condition, the load condition, and the material model are not appropriate, or in a case where the blood vessel involves great movement, there may be a problem in the convergence and the analysis stability. As described above, in conventional structural fluid analysis of blood vessels, it may be required to have large analysis resources and it may take an analysis time, or the error of the analysis result may increase, and therefore, there may be a problem in the utilization in actual clinical scenes.

BRIEF DESCRIPTION OF THE DRAWING

FIG. 3 is a figure illustrating a typical flow of structural fluid analysis processing performed under the control of a system control circuitry of FIG. 1.

FIG. 15 is a figure illustrating an example of display of a space distribution of an internal pressure which is one of mechanics indexes according to the display of FIG. 1.

FIG. 17 is a graph related to the blood pressure of the left coronary artery origin on the display of FIG. 1.

FIG. 18 is a graph related to the blood pressure around the branch point of LCX and LDA on the display of FIG. 1.

FIG. 19 is a graph related to the blood pressure change in the center line direction on the display of FIG. 1.

FIGS. 20A and 20B are figures illustrating another example of allocation of forcible displacement history performed with the dynamical model structuring circuitry of FIG. 4.

FIG. 21 is a figure illustrating another example of allocation of forcible displacement history performed with the dynamical model structuring circuitry of FIG. 4.

FIG. 22 is a figure illustrating another example of allocation of forcible displacement history performed with the dynamical model structuring circuitry of FIG. 4.

DETAILED DESCRIPTION

Figure 1:
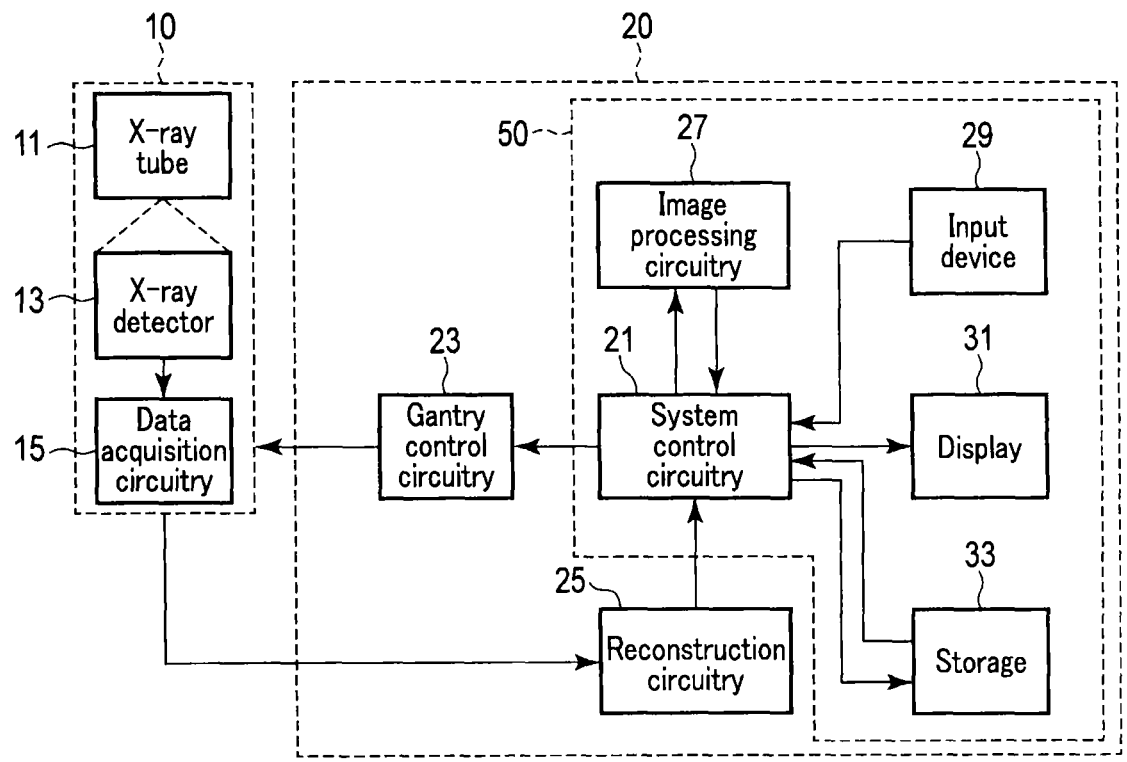
FIG. 1 is a figure illustrating a schematic block configuration of a medical image diagnosis apparatus (X-ray computer tomography apparatus) according to the present embodiment.

In general, according to one embodiment, a blood vessel analysis apparatus includes a storage, a setting circuitry, a calculation circuitry, a structuring circuitry, an identification circuitry. The storage is configured to store data of a time-series medical image of a blood vessel of a subject. The setting circuitry is configured to set an analysis target region in a blood vessel region included in the time-series medical image, and set an identification region for a latent variable in the analysis target region. The calculation circuitry is configured to calculate a time-series morphology index and a time-series shape deformation index of the analysis target region by performing image processing on the time-series medical image. The structuring circuitry is configured to temporarily structure a dynamical model of a structural fluid analysis of the analysis target region, based on the time-series morphology index, the time-series shape deformation index, and the time-series medical image. The identification circuitry is configured to identify a latent variable of the identification region so that at least one of a prediction value of a blood vessel morphology index and a prediction value of a blood flow volume index based on the temporarily structured dynamical model is in conformity with at least one of an observation value of the blood vessel morphology index and an observation value of the blood flow volume index measured in advance.

A blood vessel analysis apparatus, a medical image diagnosis apparatus, and a blood vessel analysis method according to the present embodiment will be hereinafter explained with reference to drawings.

A blood vessel analysis apparatus according to the present embodiment is a computer apparatus for performing structural fluid analysis on a blood vessel region included in a medical image generated by a medical image diagnosis apparatus. The blood vessel analysis apparatus according to the present embodiment may be incorporated into a medical image diagnosis apparatus, or may be a computer apparatus such as a work station provided separately from the medical image diagnosis apparatus. In order to explain in a specific manner, the blood vessel analysis apparatus according to the present embodiment is considered to be incorporated into the medical image diagnosis apparatus in the explanation below.

The medical image diagnosis apparatus according to the present embodiment can be applied to any type of image diagnosis apparatus provided with an image-capturing mechanism capturing an image of a subject. For example, an X-ray computer tomography apparatus (X-ray CT apparatus), a magnetic resonance diagnosis apparatus, ultrasonic diagnosis apparatus, SPECT apparatus, PET apparatus, radiological treatment apparatus, and the like can be used as necessary as the medical image diagnosis apparatus according to the present embodiment. In order to explain in a specific manner, the medical image diagnosis apparatus according to the present embodiment is considered to be an X-ray computer tomography apparatus s in the explanation below.

FIG. 1 is a schematic block configuration diagram illustrating the medical image diagnosis apparatus according to the present embodiment (X-ray computer tomography apparatus). As shown in FIG. 1, the X-ray computer tomography apparatus includes a CT gantry 10 and a console 20. The CT gantry 10 captures an image of an image-capturing portion of a subject using an X-ray in accordance with the control of the gantry control circuitry 23 of the console 20. The image-capturing portion is, for example, a heart. The CT gantry 10 includes an X-ray tube 11, an X-ray detector 13, and a data acquisition circuitry 15. The X-ray tube 11 and the X-ray detector 13 are provided on the CT gantry 10 so as to be able to rotate about a rotation axis Z. The X-ray tube 11 emits an X-ray onto a subject in which a contrast medium is injected. The X-ray detector 13 detects the X-ray generated from the X-ray tube 11 and transmitted through the subject, and generates an electric signal in accordance with the intensity of the detected X-ray. The data acquisition circuitry 15 reads the electric signal from the X-ray detector 13 and converts the electric signal into digital data. A set of digital data for each view is referred to as a raw data set. A time-series raw data set of multiple scan times are transmitted by a non-contact data transmission apparatus (not shown) to the console 20.

The console 20 has a system control circuitry 21 as a center, and includes a gantry control circuitry 23, a reconstruction circuitry 25, an image processing circuitry 27, an input device 29, a display 31, and a storage 33.

The gantry control circuitry 23 controls each apparatus in the console 20 in accordance with a scan condition set with the input device 29 by the user.

The reconstruction circuitry 25 generates data of a CT image of a subject based on a raw data set. More specifically, first, the reconstruction circuitry 25 generates a projection data set by applying pre-processing to the raw data set. The pre-processing includes logarithmic transformation, non-uniform correction, calibration correction, and the like. Subsequently, the reconstruction circuitry 25 generates data of a CT image by applying image reconfiguration processing to the projection data set. Existing algorithms such as analytic image reconfiguration methods such as filtered back projection (FBP) method and successive approximation image reconfiguration such as maximum likelihood expectation maximization (ML-EM) method and ordered subset expectation maximization (OS-EM) method can be applied as the image reconfiguration algorithm. In the present embodiment, the reconstruction circuitry 25 generates time-series data of CT images on the basis of time-series projection data set. The CT image includes pixel regions of blood vessels imaged with the contrast medium (hereinafter referred to as blood vessel regions). It should be noted that the CT image may be slice data representing two-dimensional space distribution of CT values, or may be volume data representing three-dimensional space distribution of CT values. Hereinafter, a CT image is considered to be volume data. The data of the time-series CT image are stored in the storage 33.

The image processing circuitry 27 executes structural fluid analysis by structuring a dynamical model based on the time-series CT images. The details of the processing of the image processing circuitry 27 will be explained later.

The input device 29 receives various kinds of commands and information inputs from the user. A keyboard, a mouse, a switch, and the like can be used as the input device 29.

The display 31 displays various kinds of information such as a CT image, a structural fluid analysis result, and the like. For example, a CRT display, a liquid crystal display, an organic EL display, a plasma display and the like can be used as the display 31 as necessary.

The storage 33 is constituted by various kinds of storage media such as a hard disk apparatus. The storage 33 stores various kinds of data such as time-series projection data, time-series CT image data, and the like. For example, the storage 33 stores time-series CT image data in a medical image file format based on digital imaging and communications in medicine (DICOM) specification. The storage 33 may store medical data collected by an external device in association with time-series CT image data in a medical image file.

The system control circuitry 21 includes a central processing circuitry (CPU), read only memory (ROM), a random access memory (RAM). The system control circuitry 21 functions as the center of the X-ray computer tomography apparatus. The system control circuitry 21 executes the blood vessel structure analysis processing according to the present embodiment by executing the blood vessel analysis program stored in the ROM and the RAM.

It should be noted that the system control circuitry 21, the image processing circuitry 27, the input device 29, the display 31, and the storage 33 constitute the blood vessel analysis apparatus 50. Like the present embodiment, the blood vessel analysis apparatus 50 may be incorporated into the medical image diagnosis apparatus (X-ray computer tomography apparatus), or may be a computer apparatus provided separately from the medical image diagnosis apparatus. The blood vessel analysis apparatus 50 is provided separately from the medical image diagnosis apparatus, the blood vessel analysis apparatus 50 may collect medical data such as time-series CT images via a network from the medical image diagnosis apparatus and a picture archiving and communication systems (PACS).

Subsequently, an example of operation of the present embodiment will be explained in details. The blood vessel analysis apparatus, medical image diagnosis apparatus, and blood vessel analysis method according to the present embodiment can adopt, as the analysis target, blood vessels in any portion of the human body such as a heart blood vessel, a carotid artery, and a cerebral artery. However, in order to explain in a specific manner, analysis target according to the present embodiment is considered to be a blood vessel in the heart in the explanation below.

Examples of blood vessels of the heart include a coronary artery and a pulmonary artery. The coronary artery starts from the coronary artery origin of the pulmonary artery, runs on the cardiac muscle surface and enter into the endocardium side from the epicardium side. The coronary artery branches into numerous number of capillaries at the endocardium of the cardiac muscle. After the coronary artery branches into numerous number of capillaries, the numerous number of capillaries are united again to form a great cardiac vein and connected to the coronary sinus. Unlike other organs, the coronary vascular system is characterized in that the perfusion is to be ensured in dynamics change of contraction and relaxation of the cardiac muscle.

The feature of the coronary blood flow is such that more blood flows when the perfusion pressure decreases in the left ventricle diastole phase than in the contraction phase in which the internal pressure of the origin of the coronary artery increases due to the mechanical bloodstream hindering effect due to the cardiac muscle contraction. For this reason, a normal coronary artery blood flow rate waveform has a bimodal feature including a contraction phase and a diastole phase, and the diastole phase bloodstream is superior. It is known that bloodstream waveforms peculiar to diseases are found, e.g., in the hypertrophic cardiomyopathy and the pulmonary stenosis, a reverse propagating wave is found in the contraction phase, and in the pulmonary regurgitation, the contraction phase forward wave increases. The forward propagating waveform in the diastole phase is closely related to the left ventricle diastolic function, and more specifically, the forward propagating waveform in the diastole phase is closely related to the left ventricle relaxation. In an example of the delay in the left ventricle relaxation, the peak of the diastole phase waveform is shifted to a later point in time, and the deceleration leg tends to be milder. In this kind of cases, the coronary blood flow of the diastole phase cannot sufficiently increase during the fast heart rate, and this may promote myocardial ischemia.

In the anatomy, a coronary perfusion pressure equivalent to the pulmonary artery is applied to the left and coronary arteries branched from the origin of the pulmonary artery, and more specifically, the pressure of the origin pulmonary artery where the coronary arteries are branched is applied to the left and coronary arteries branched from the origin of the pulmonary artery, so that the coronary blood flow is generated. In order to determine the coronary blood flow, not only the driving pressure which is the pulmonary artery pressure but also coronary vascular resistance are important. In thick coronary blood vessels of 140 to 180 μm or more, about 20% of the coronary vascular resistance is said to exist, and in microvessels of 100 to 150 μm or less, most of the remaining resistance component is said to exist. Therefore, when there is not any so-called coronal artery stenosis and the like, the resistance value depends on the tonic (tonus) of coronary microvessels.

The blood vessel resistance factors include blood vessel characteristics, arteriosclerosis, vessel stenosis, and blood viscosity, mechanical factors. The tonus of the coronary microvessel is defined by blood vessel characteristics, cardiac muscle metabolism (cardiac muscle oxygen consumption), neurohumor factors, mechanical factor, various kinds of vasoactive intestinal substance body fluid factors, and blood viscosity, and is further affected by various kinds of pathologic changes including cardiac enlargement, coronary arteriosclerosis, and the like, and causes coronary circulation disturbance.

The coronary artery bloodstream pulsation is affected by the pulsation pattern of the coronary artery bloodstream, the control of the bloodstream in the cardiac muscle with the cardiac muscle contraction, and reaction of the blood vessel in the cardiac muscle in response to mechanical stimulation. The order in which the bloodstream is hindered by the cardiac muscle contraction includes an increase in the cardiac muscle internal pressure, a change of the blood vessel capacity in the cardiac muscle, and oppression of the blood vessel capacity in the cardiac muscle. The bloodstream defining factors in the cardiac muscle diastole phase includes the coronary artery pressure in the diastole phase, the blood vessel external force in the diastole phase, the heart rate, the ratio of the diastole phase with respect to the cardiac cycle, and the cardiac muscle relaxation.

The blood vessel analysis apparatus 50 according to the present embodiment structures the dynamical model based on the time-series CT images, and executes the structural fluid analysis on the blood vessel of the heart by using the dynamical model, and accurately calculates the amount of flow the dynamics index and the blood vessel flow volume index in the blood vessel. In order to accurately calculate the dynamics index and the blood vessel flow volume index, it is necessary to allocate a highly accurate latent variable to the dynamical model. When the blood vessel analysis apparatus 50 structures the dynamical model, the blood vessel analysis apparatus 50 statistically identifies a latent variable by performing inverse analysis on the initial dynamical model. Therefore, the blood vessel analysis apparatus 50 can accurately determine the latent variable. The dynamics index means the dynamics index about the blood vessel wall. The dynamics index about the blood vessel wall is classified into, for example, an index of displacement of a blood vessel wall, an index of stress and distortion applied to a blood vessel wall, an index of internal pressure distribution applied to an intravascular lumen, an index of material characteristics representing the hardness of the blood vessel, and the like. The index of material characteristics representing the hardness of the blood vessel includes, e.g., an average inclination of a curved line representing a relationship of stress and distortion of a blood vessel tissue. The blood flow volume index means an index of hemodynamics about blood flowing in a blood vessel. Examples of blood vessel flow volume indexes include the amount of flow of blood, the flow rate of blood, viscosity of blood, and the like.

The latent variable includes, for example, at least one of a parameter of a material model such as a material constitutive equation of blood vessel or a material constitutive equation of blood (for example, Young's modulus, Poisson's ratio, and the like), a load condition parameter such as an internal pressure distribution applied to an intravascular lumen, a boundary condition parameter of structure analysis and fluid analysis, and a variation distribution parameter related to uncertainty of a time-series morphology index and shape deformation index. In this case, a variation distribution parameter related to uncertainty of time-series morphology index and shape deformation index is such that various kinds of uncertainties are expressed as probability distributions in view of the fact that medical image data include variation distribution caused by noise of each CT value, probability distribution caused by ambiguity of a boundary threshold value of a living tissue, and the like. Examples of various kinds of uncertainties include uncertainty in a space coordinate of boundary coordinates of blood vessel tissue and blood and feature points (such as a blood vessel branching portion, a contrast medium distribution arrangement, and the like), uncertainty of a geometric structure parameter (lumen radius and the like in a cross section perpendicular to a center line), and uncertainty of a medical image data itself (such as a CT value, a boundary threshold value, and the like).

The dynamical model is a numerical model expressing behavior of a blood vessel and blood. The dynamical model has different types according to schemes of structural fluid analysis. For example, the dynamical model is classified into continuum dynamical model and simplified dynamical model. The continuum dynamical model is used for, for example, finite element method (FEM) and boundary element method. The simplified dynamical model is classified into, for example, a material dynamical model based on material dynamics and a fluid dynamical model based on flow studies. Unless otherwise specified in the following explanation, the type of the dynamical model is not particularly limited. The initial dynamical model is considered to mean a dynamical model allocated with a sampling set about parameters of latent variables that can be obtained from a variable range and probability distribution of latent variables (a set of combination of parameters).

Figure 2:
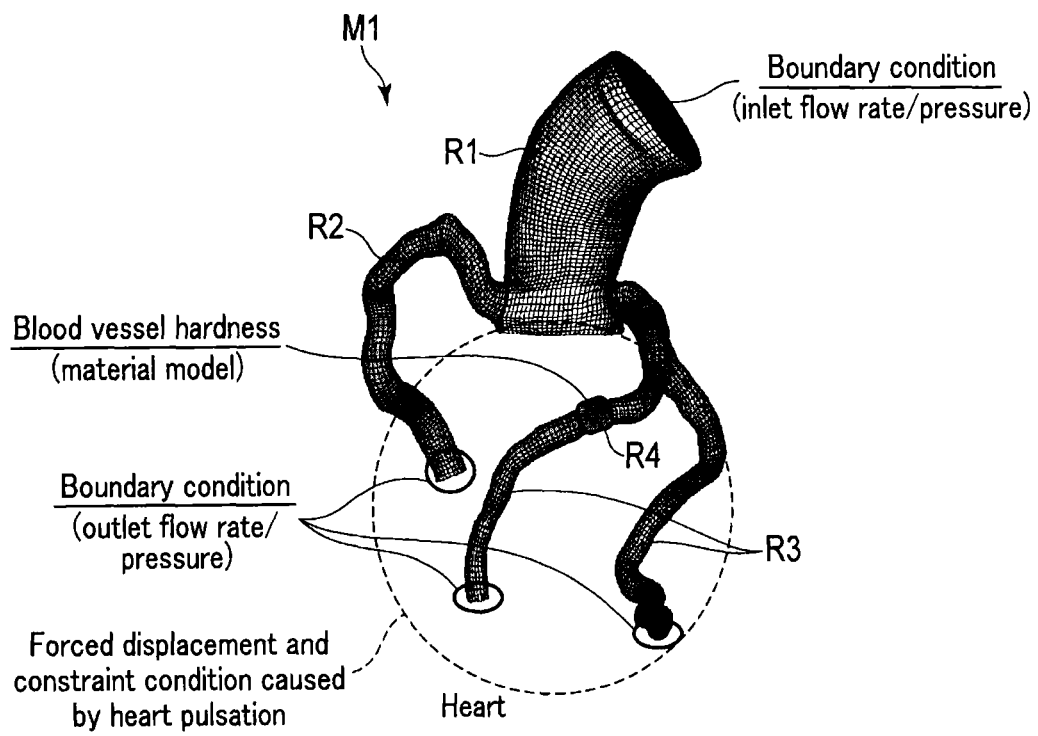
FIG. 2 is a figure illustrating an example of a dynamical model of a target region of a structural fluid analysis according to the present embodiment.

FIG. 2 is a figure illustrating an example of a dynamical model M1 of a target region of structural fluid analysis (hereinafter referred to as an analysis target region). As shown in FIG. 2, the dynamical model M1 includes a pulmonary artery region R1, a right coronary artery region R2, and a left coronary artery region R3. The blood flows from the pulmonary artery to the right coronary artery or the left coronary artery.

As shown in FIG. 2, in the dynamical model M1, the end at the side of the origin of the pulmonary artery is set as the entrance of the bloodstream, and the end of the right coronary artery region and the end of the left coronary artery region are set as the exit of the bloodstream. A boundary condition is set at each of the entrance and the exit. The boundary condition about the entrance includes, for example, the flow rate of the bloodstream, or the pressure generated by the bloodstream at the entrance, or the rate of change thereof. The boundary condition about the exit includes, for example, the flow rate of the bloodstream, or the pressure generated by the bloodstream at the exit, or the rate of change thereof. The deformation of the pulmonary artery, the right coronary artery, and the left coronary artery depends on various factors such as mechanical action to the blood vessel wall caused by the bloodstream, mechanical action to the blood vessel wall caused by the pulsation of the heart (external force), the load condition of the blood vessel cross section boundary, the material model of the blood vessel wall, non-stress state of the blood vessel, geometric shape of the blood vessel wall, and the like. In this case, the mechanical action to the blood vessel wall caused by the bloodstream includes, for example, the internal pressure caused by the bloodstream and the shear stress caused by the bloodstream. Due to the internal pressure caused by the bloodstream, deformation occurs in the blood vessel circle or the direction perpendicular to the intravascular lumen surface. With the mechanical action to the blood vessel wall caused by the pulsation of the heart and the shear stress caused by the bloodstream, the deformation of the blood vessel such as expansion and contraction, twisting, bending, and the like in the blood vessel center line direction is allocated, as the load condition, to the pulmonary artery region R1, the right coronary artery region R2, and the left coronary artery region R3. More specifically, the deformation of the blood vessel such as expansion and contraction, twisting, bending, and the like in the blood vessel center line direction is expressed by a forcible displacement (movement vector and rotation displacement) or a temporal change of a load vector. The deformation in the blood vessel circle or the direction perpendicular to the lumen surface based on the internal pressure caused by the bloodstream is allocated to the intravascular lumen as a temporal change of the pressure distribution.

The displacement constraint condition due to forcible displacement is allocated to the pulmonary artery region R1, the right coronary artery region R2, and the left coronary artery region R3 in the structural fluid analysis. Therefore, the deformation freedom degree of the blood vessel wall in the structural fluid analysis can be reduced, and the calculation convergence can be stabilized, and the analysis time can be reduced.

For example, the deformation degree of the shape of the blood vessel depends on the material of the blood vessel wall. For this reason, the material model is allocated to the pulmonary artery region R1, the right coronary artery region R2, and the left coronary artery region R3. The deformation degree of the shape of the blood vessel also depends on the non-stress state of the blood vessel. The residual stress distribution of the blood vessel may be allocated as the initial value of the load condition. A node-set obtained by discretizing the space of the dynamical model for numerical calculation of the blood vessel analysis target and an element-set constituted by nodes is divided into an region where analysis conditions such as a material model, a boundary condition, a load condition, and the like are identified and an region where analysis conditions such as a material model, a boundary condition, a load condition, and the like are not identified. A displacement constraint condition of a forcible displacement history is allocated to nodes in the identification region of the analysis condition, and in the identification region of the material model, a displacement constraint condition of a forcible displacement history is allocated to only the nodes of the blood vessel wall surface (external surface), and in the blood vessel wall, a displacement freedom degree is allocated, and no displacement constraint is allocated. Therefore, the deformation freedom degree of the structural fluid analysis can be suppressed, and the analysis can be performed in a stable and efficient manner. However, a dummy element set for buffer may be provided on the blood vessel wall surface, and a forcible displacement may be given to the nodes on the surface. Therefore, in a case where there is a protrusion due to a plaque and the like on the intravascular lumen or in a case where the load due to the internal pressure such as a blood vessel branching portion affects deformation outside of the cross section in the center line direction, the load vector applied to the blood vessel and the internal pressure can be separated and identified in view of the morphology indexes of not only the intravascular lumen but also the blood vessel wall. A fat layer of a wall surface is simulated in terms of physiology, and on the other hand, in the numerical calculation, a forcible displacement is given to the blood vessel wall surface, so that there is an effect of avoiding generation of a high stress different from the reality in a local manner in the blood vessel wall.

The parameters about latent variables such as the material model, the boundary condition, and the load condition are identified by the inverse analysis (statistical identification processing) based on the dynamical model explained later. The accurate latent variables identified by the inverse analysis allocated to the dynamical model. With the dynamical model to which accurate latent variables allocated, the hemodynamics analysis can be executed based on structural fluid analysis or fluid analysis or structure analysis or image analysis in view of the effect to the analysis target blood vessel region due to the external factors such as the blood vessel and the heart outside of the analysis target blood vessel region. When the blood vessel analysis apparatus 50 structures the dynamical model, the blood vessel analysis apparatus 50 can solve the following four difficulties associated with a conventional example using the identification of the latent variables with the inverse analysis. Difficulty 1: identification method of the material model of the coronary artery. Difficulty 2: incorporation of the effect of deformation of the shape of the heart to the coronary artery. Difficulty 3: identification method of the boundary condition of the coronary artery. Difficulty 4: image analysis and structural fluid analysis using the blood vessel shape having variation based on uncertainty of medical image data. By overcoming the four difficulties, the blood vessel analysis apparatus 50 achieves the improvement of the analysis accuracy as compared with a conventional blood vessel structural fluid analysis in which latent variables are not identified with the inverse analysis.

Figure 4:
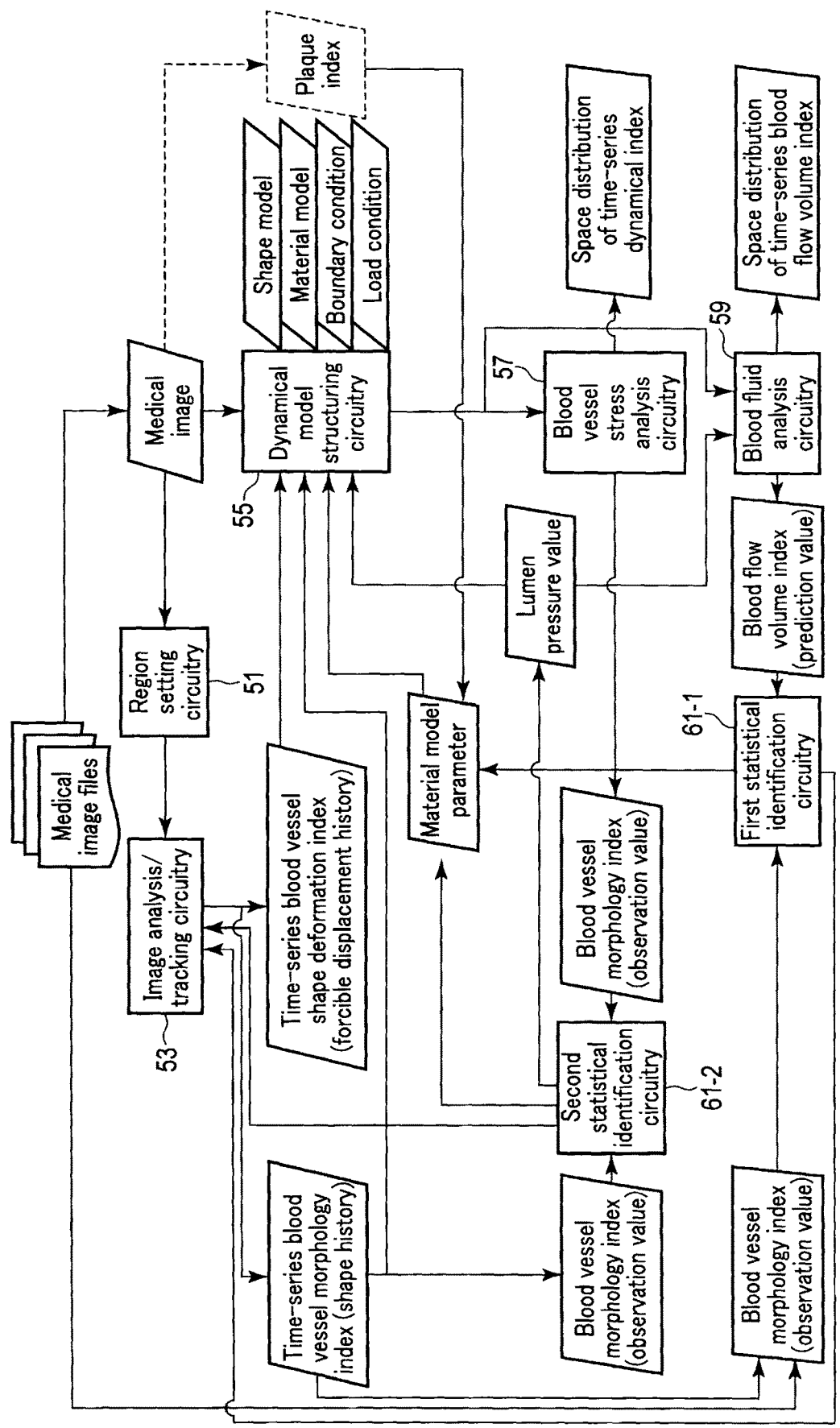
FIG. 4 is a figure illustrating a block configuration of the image processing circuitry of FIG. 1.

Subsequently, the details of the structural fluid analysis processing according to the present embodiment will be explained. FIG. 3 is a figure illustrating a typical flow of structural fluid analysis processing performed under the control of the system control circuitry 21 according to the present embodiment. FIG. 4 is a figure illustrating a block configuration of the image processing circuitry 27.

As shown in FIG. 3, in the structural fluid analysis processing, first, the system control circuitry 21 reads a medical image file of processing target from the storage 33, and provides the medical image file to the image processing circuitry 27. The medical image file includes not only data of time-series CT images but also data of pressure values about the intravascular lumen about the subject, data of observation value of the blood flow volume index, and the plaque index. Instead of the CT image, an MRI image and an ultrasonic echo image may also be used. The data of the time-series CT images are data representing three-dimensional space distribution of time-series CT values. The time-series CT images include, for example, 20 CT images per cardiac beat, and more specifically, the time-series CT images include, for example, CT images for about 20 cardiac phases.

As shown in FIG. 3, the system control circuitry 21 causes the image processing circuitry 27 to perform the region setting processing (step S1). In step S1, the region setting circuitry 51 of the image processing circuitry 27 sets the analysis target region of the structural fluid analysis in the blood vessel region included in the time-series CT image. The analysis target region is set in any given portion of the blood vessel region about the coronary artery. For example, the region setting circuitry 51 sets an analysis target region and an identification target region to a blood vessel region according to a command given with the input device 29 by the user or the image processing.

Figure 5:
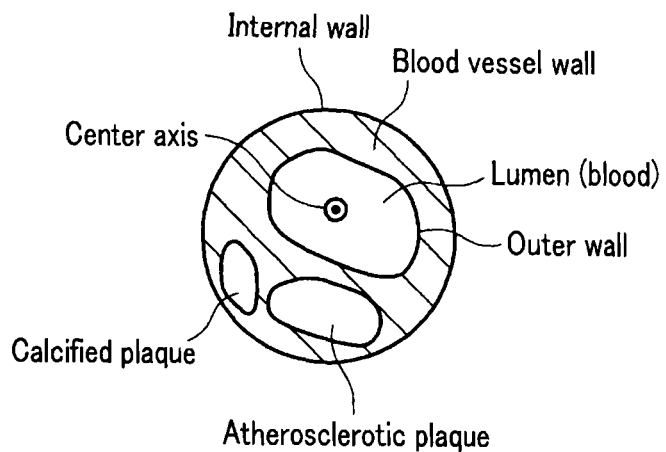
FIG. 5 is a figure schematically illustrating a cross section perpendicular to a center line of a blood vessel.

In this case, the structure of the blood vessel will be explained with reference to FIG. 5. FIG. 5 is a figure schematically illustrating a cross section perpendicular to the center line of the blood vessel (hereinafter referred to as a blood vessel cross section). As shown in FIG. 5, the blood vessel includes a tube-like blood vessel wall. The center axis of the blood vessel wall will be referred to as a center line. The internal wall of the blood vessel wall will be referred to as a lumen. Blood flows to the lumen. The border between the lumen and the blood vessel wall is referred to as a blood vessel wall. Outside of the blood vessel wall, perivascular tissues such as cardiac muscles are distributed. The border between the blood vessel wall and the perivascular tissue is referred to as a blood vessel external wall. Inside of the blood vessel wall, a plaque may be generated. As shown in FIG. 5, the plaque is classified into, for example, calcified plaque, atherosclerotic plaque, and the like. The atherosclerotic plaque may be referred to as an unstable plaque. The atherosclerotic plaque is soft, and the blood vessel wall may break and exude to the inside of the blood vessel as a thrombus. Therefore, it is useful to find the property of the plaque in a clinical manner. The property and the existing region of the plaque may be identified by the plaque index included in the medical image file. The plaque index can be relatively determined by, for example, the size of the CT value normalized based on the CT value of the bone. However, it is easy to analyze the deformation characteristics and the hardness of the plaque inside of the blood vessel.

When step S1 is performed, the system control circuitry 21 causes the image processing circuitry 27 to perform image analysis/tracking processing (step S2). In step S2, the image analysis/tracking processing circuitry 53 of the image processing circuitry 27 performs image processing on the time-series CT images to calculate time-series blood vessel morphology index and the time-series blood vessel shape deformation index. More specifically, the image analysis/tracking processing circuitry 53 performs the image analysis processing on the time-series CT image to calculate the time-series blood vessel morphology index, and performs tracking processing on the time-series CT image to calculate the time-series blood vessel shape deformation index.

More specifically, the image analysis/tracking processing circuitry 53 extracts the blood vessel region from each CT image in the image analysis processing, and identifies a pixel region about a lumen of a blood vessel (hereinafter referred to as an intravascular lumen region) and a pixel region about a blood vessel wall (hereinafter referred to as a blood vessel wall region). The image analysis/tracking processing circuitry 53 identifies, blood vessel morphology indexes, three-dimensional coordinates of multiple pixels on an region where a cross section perpendicular to a center line of a blood vessel or a plane perpendicular to an intravascular lumen surface crosses an intravascular lumen, a blood vessel wall, and plaque region. It should be noted that the blood vessel morphology index is not limited to a three-dimensional coordinate, and may be various kinds of geometric indexes. For example, the radius, the diameter, and zero-degrees direction vector of the intravascular lumen with a regular interval of angles in the cross section perpendicular to the center line, or an average region size and an average radius with respect to the whole angle in the cross section, or the intravascular lumen capacities enclosed by multiple cross sections perpendicular to the center line direction, or the blood vessel wall capacities and the plaque capacities enclosed by multiple cross sections perpendicular to the lumen surface can be used as geometric indexes according to the present embodiment.

In the tracking processing, the image analysis/tracking processing circuitry 53 sets multiple feature points such as feature points, feature shapes, representative points, and pixels according to the image processing or the command given with the input device 29 by the user. More specifically, the feature points are set in a blood vessel region, a blood region, a contrast medium region, a proton region, and the like. For example, the image analysis/tracking processing circuitry 53 sets feature point sets such as a blood vessel branching portion and a feature shape of a surface. The blood vessel wall surface of the dynamical model, the inside of the blood vessel wall, or the temporal change of the displacement of the node in the intravascular lumen are calculated by the interpolation processing and the like from the displacement data of the feature point set obtained from the tracking processing of the image analysis/tracking processing circuitry 53 at each time (each cardiac phase), and the calculated temporal change is allocated as the forcible displacement. For example, the image analysis/tracking processing circuitry 53 defines the node on the blood vessel center line in the dynamical model. The image analysis/tracking processing circuitry 53 may extract the expansion and contraction in the center line direction of the blood vessel and deformation about twisting and bending from the temporal change from the blood vessel wall surface of the dynamical model, the inside of the blood vessel wall, or the displacement at the node of the intravascular lumen, and this may be expressed as being given as the forcible displacement of the node in the cross section perpendicular to the blood vessel center line and the center line. As described above, the forcible displacement data of the node at each time for the dynamical model (forcible displacement history) are identified as the blood vessel shape deformation indexes.

Figure 6:
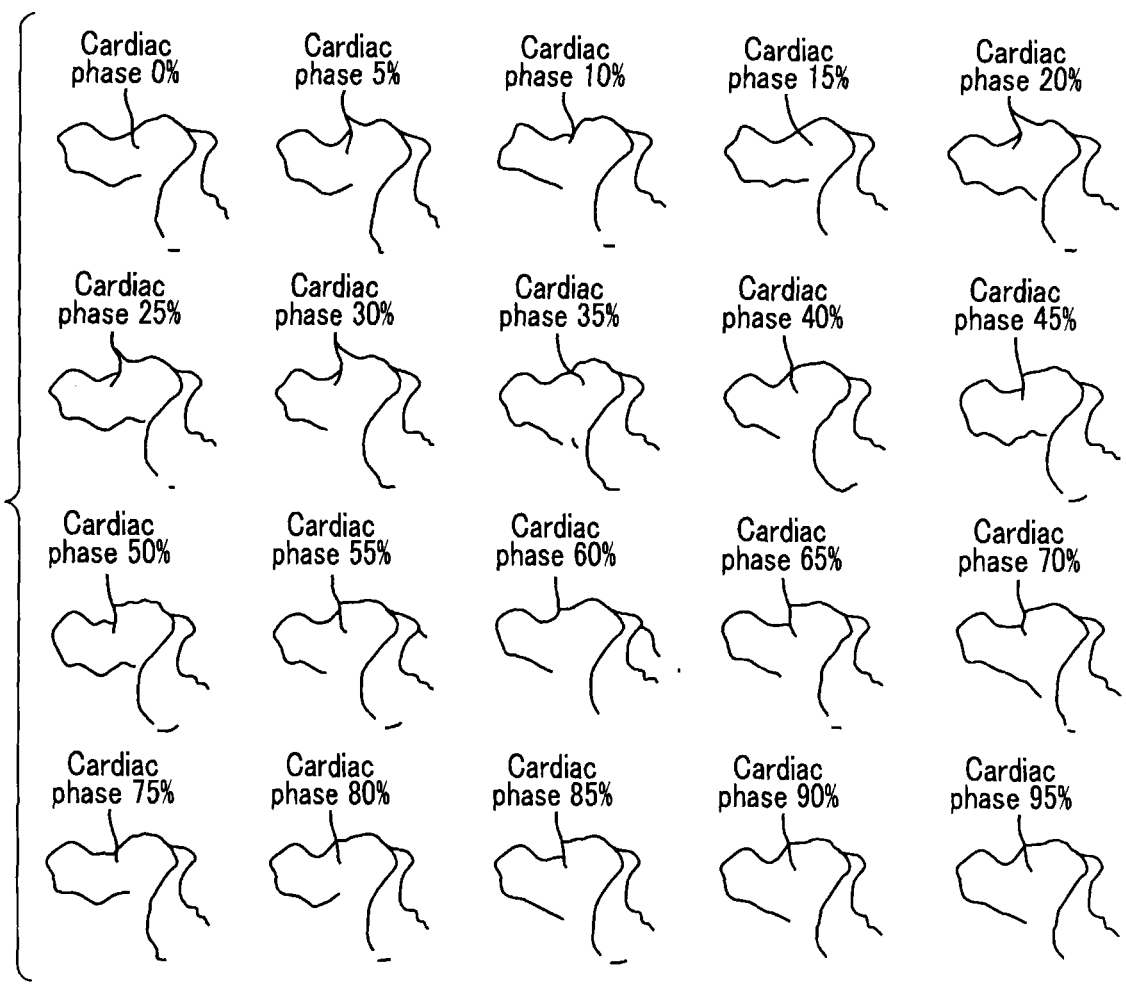
FIG. 6 is a figure illustrating a time change of an aspect of a blood vessel center line used for image tracking processing performed with image analysis/tracking processing of FIG. 4.

Hereinafter, the image analysis/tracking processing will be explained with reference to FIG. 6, FIG. 7, and FIG. 8. FIG. 6 is a figure illustrating a temporal change of a mode of a blood vessel center line. As shown in FIG. 6, for example, the time-series medical images include 20 CT images per cardiac beat. More specifically, CT images are considered to be obtained with an interval of 5% from the cardiac phases 0% to 95%. The center line of the blood vessel region is extracted from each CT image by the image analysis/tracking processing circuitry 53. As shown in FIG. 6, the mode of the center line changes in accordance with the elapse of the cardiac phase.

Figure 8:
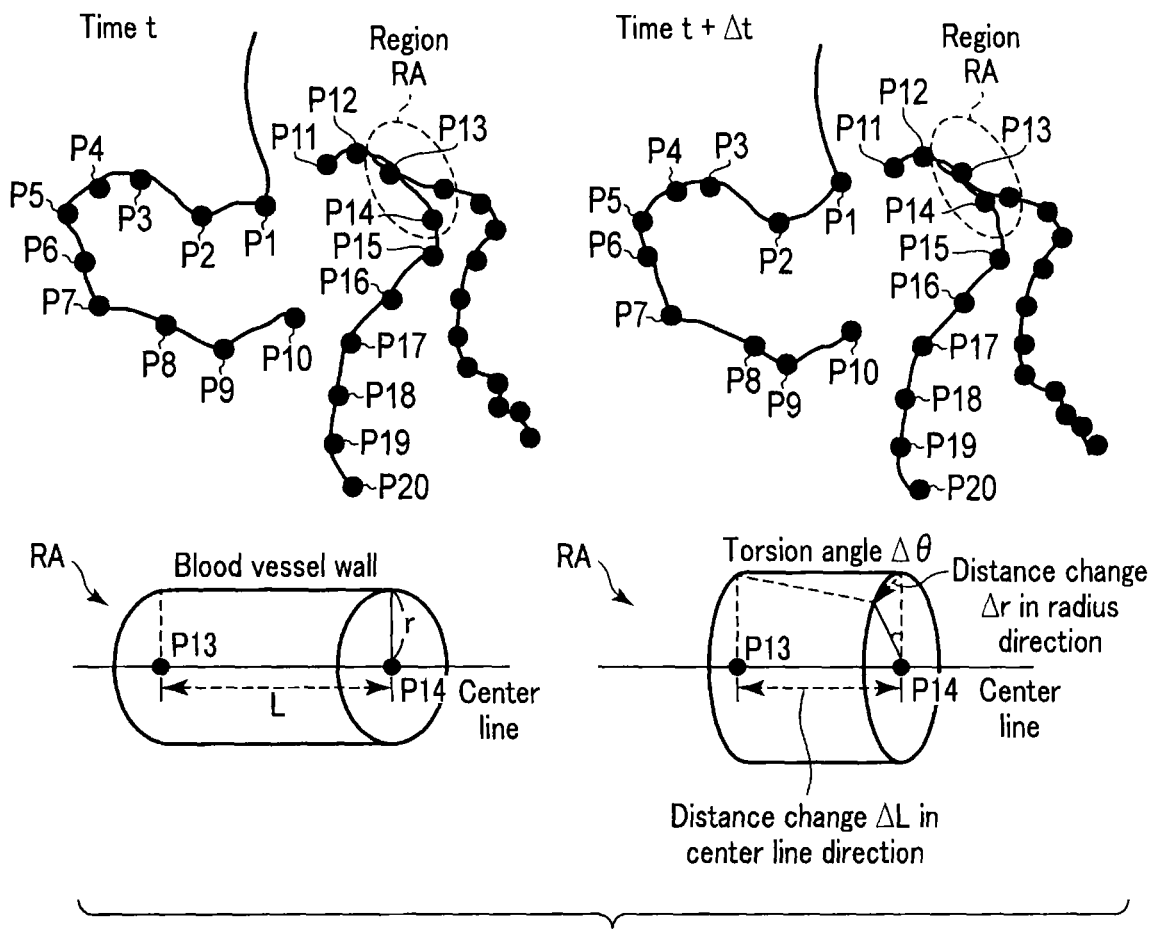
FIG. 8 is a figure for explaining image tracking processing according to the image analysis/tracking processing of FIG. 4, and is a figure illustrating an example of tracking processing between a time t and a time t+Δt.

FIG. 8 is a figure illustrating an example of tracking processing between a time t and a time t+Δt. As shown in FIG. 8, the nodes of the dynamical model from P1 to P10 are set on the blood vessel center lines, and mechanically connected to the nodes of the dynamical model of the blood vessel on each cross section. However, they are independent from the nodes of the dynamical model of the blood. Based on the displacement data of the feature points of the blood vessel, the displacement data of the nodes of P1 to P20 on the blood vessel center line are calculated by processing such as interpolation, and the forcible displacement is considered to be set for each node. In order to explain the blood vessel shape deformation index and the blood vessel morphology index, a local blood vessel region RA defined by the node P13 and the node P14 will be considered. At a time t, the distance between the node P13 and the node P14 in the center line direction is considered to be L, and the radius in the blood vessel region is considered to be r. Forcible displacement such as expansion and contraction, twisting, and bending in the blood vessel center line direction of the node P13 and the node P14 is extracted from the image analysis/tracking processing circuitry 53, so that the forcible displacement at the node P13 (the movement displacement in the three-dimensional space and the rotation displacement in the center line direction) and the forcible displacement at the node P14 (the movement displacement in the three-dimensional space and the rotation displacement in the center line direction) are calculated.

Figure 7:
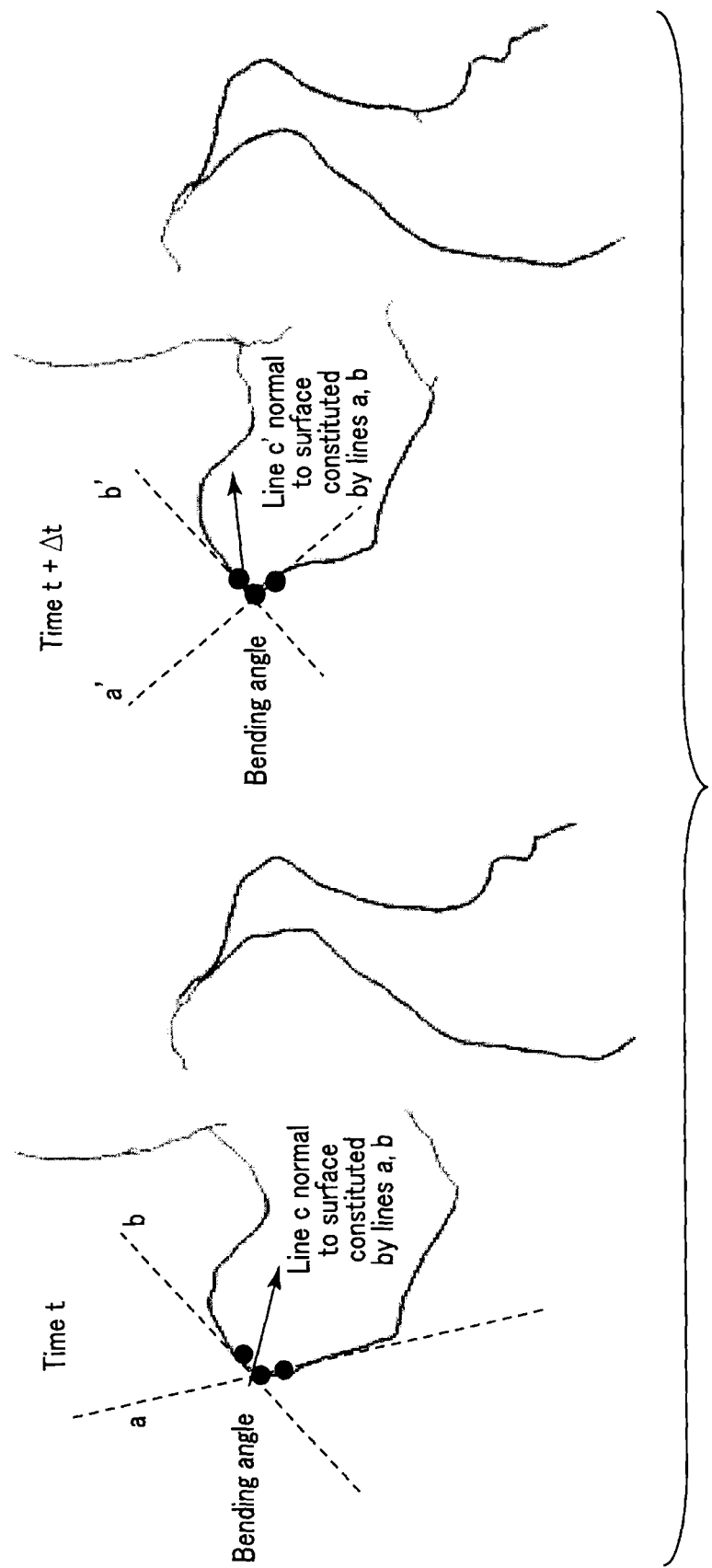
FIG. 7 is a figure illustrating an example of calculation of bending deformation and rotation displacement of a blood vessel center line according to the image analysis/tracking processing of FIG. 4.

FIG. 7 is a figure illustrating an example of calculation of bending deformation and rotation displacement of a blood vessel center line. As shown in FIG. 7, for example, the bending angle may be calculated from a change of a vector c normal to the surface constituted by lines a and b.

As shown in FIGS. 7 and 8, the image analysis/tracking processing circuitry 53 calculates the forcible displacement at each node on the center line (the movement displacement in the three-dimensional space and the rotation displacement in the center line direction) based on the coordinate and the movement vector of the feature point, and calculates the blood vessel shape deformation index. For example, the image analysis/tracking processing circuitry 53 calculates a time change of a coordinate difference of two adjacent nodes is calculated as the expansion and contraction distance $\Delta L$ in the center line. With regard to the node on each center line, the image analysis/tracking processing circuitry 53 calculates a time change of a distance between the node in question and another node on the blood vessel region cross section including the node in question (the node in the intravascular lumen or the blood vessel wall or the plaque region) as the expansion and contraction distance $\Delta r$ in the radius direction. With regard to each feature point, the image analysis/tracking processing circuitry 53 calculates a torsion angle $\Delta\theta$ in the center line direction of the node in question on the center line based on the coordinates and the movement vectors of multiple feature points in proximity to the feature point.

The image analysis/tracking processing circuitry 53 may calculate the average flow rate or the average amount of flow in the flow rate or center line direction cross section as the blood flow volume index with the image tracking of the contrast medium and the proton of the blood region.

The blood vessel shape deformation index is used as the forcible displacement in the dynamical model. Hereinafter the time-series blood vessel morphology index will be referred to as a shape history, and the time-series blood vessel shape deformation index will be referred to as a forcible displacement history.

When step S2 is performed, the system control circuitry 21 causes the image processing circuitry 27 to perform the structuring processing (step S3). In step S3, the dynamical model structuring circuitry 55 of the image processing circuitry 27 temporarily structures the dynamical model of the analysis target region based on the shape history (time-series blood vessel morphology index) and the forcible displacement history (time-series blood vessel shape deformation index) and the time-series medical image (DICOM data such as CT image, MRI image, ultrasonic echo image, and the like). The dynamical model is a numerical model about the analysis target region for performing the structural fluid analysis.

Hereinafter, step S3 will be explained in details. First, the dynamical model structuring circuitry 55 structures the shape model for solving the dynamical model (mathematical model) based on the medical image and the shape history. The shape model schematically expresses the geometric structure of the blood vessel region at each time. The shape model is classified into, for example, multiple discretized regions. The vertex of each of the discretized regions is referred to as a node. The dynamical model structuring circuitry 55 may structure the shape model for each time based on the blood vessel region and the blood vessel morphology index included in the medical image for each time, and may structure the shape model for each time based on the blood vessel region and the blood vessel morphology index included in the medical image of a particular time phase. For example, when it is assumed that there is no residual stress in the blood vessel corresponding to the analysis target region in the initial load state, a time phase at which the blood vessel corresponding to the analysis target region is most greatly contracted in the time phase of the non-stress state is assumed to be a non-stress state.

Figure 9:
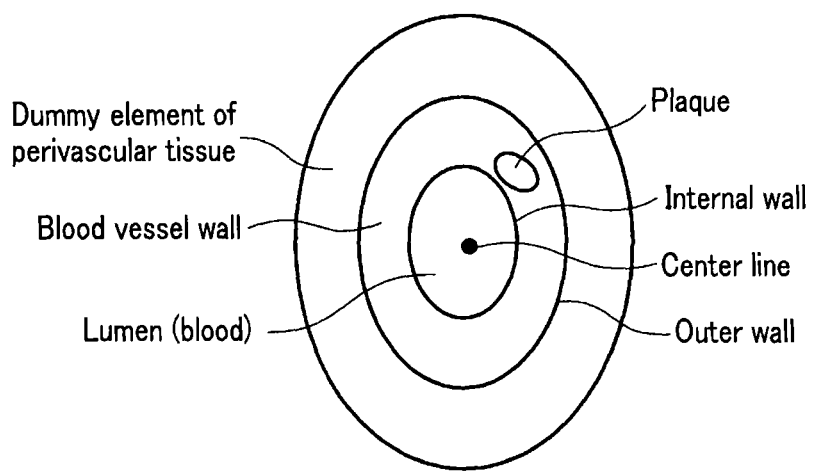
FIG. 9 is a figure illustrating a cross section perpendicular to a center line of a shape model structured by a dynamical model structuring circuitry of FIG. 4.

FIG. 9 is a figure illustrating a cross section perpendicular to a center line of a shape model. As shown in FIG. 9, the shape model has an intravascular lumen region and a blood vessel wall region which regionrranged from the center line to the outside. When there is a plaque, a plaque region may be provided in the blood vessel wall region. When the effect to the blood vessel by the perivascular tissue is taken into consideration, the dummy element of the perivascular tissue may be provided outside of the blood vessel wall region.

When the shape model is structured, the dynamical model structuring circuitry 55 sets the sampling value about the parameter of the latent variable obtained from the variable range and the probability distribution of each latent variable (for example, sampling from a set of combination of parameters based on Markov chain Monte Carlo method and the like) to the dynamical model. For example, as shown in FIG. 2, the dynamical model structuring circuitry 55 sets the region of the identification target of the boundary condition about the entrance (hereinafter referred to as a boundary condition identification region) at the end of the pulmonary artery region R1 at the side of the origin of the pulmonary artery, and sets the boundary condition identification region about the exit at the end of the right coronary artery region R2 and the end of the left coronary artery region R3. The dynamical model structuring circuitry 55 allocates the sampling value about the parameter of the boundary condition obtained from the variable range and the probability distribution of the boundary condition to each boundary condition identification region. The dynamical model structuring circuitry 55 also sets the region of the identification target of the material model (hereinafter referred to as a material model identification region) and the region of the identification target of the load condition (hereinafter referred to as a load condition identification region) in the pulmonary artery region R1, the right coronary artery region R2, and the left coronary artery region R3. The dynamical model structuring circuitry 55 allocates the sampling value about the parameter of the material model obtained from the variable range and the probability distribution of the material model to each material model identification region, and allocates the sampling value about the parameter of the load condition obtained from the variable range and the probability distribution of the load condition to each load condition identification region. In the blood vessel, even when the amount of flow is zero, it is said that there is a residual stress. For example, the dynamical model structuring circuitry 55 may allocate the residual stress in a case where the amount of flow is zero to the analysis target region as the initial value of the load condition. The dynamical model structuring circuitry 55 may set an region of identification target of the geometric structure (hereinafter referred to as a geometric structure identification region) to a portion where there is uncertainty in the geometric structure. It should be noted that the parameter of the geometric structure is a variation distribution parameter related to uncertainty of the geometric structure, or a variation distribution parameter involved in the medical image data, and may be, e.g., a variation distribution of the boundary threshold value of the living tissue and the variation distribution of each CT value. The dynamical model structuring circuitry 55 may set the material model in the plaque region, the details of which will be explained later. The details of the material model will be explained later.

When the shape model is structured, the dynamical model structuring circuitry 55 allocates the time-series blood vessel shape deformation index calculated in step S2 to the shape model, and more specifically, the dynamical model structuring circuitry 55 allocates the forcible displacement history to the shape model. The shape model to which the latent variable and the forcible displacement history regionllocated will be referred to as a dynamical model.

Figure 10:
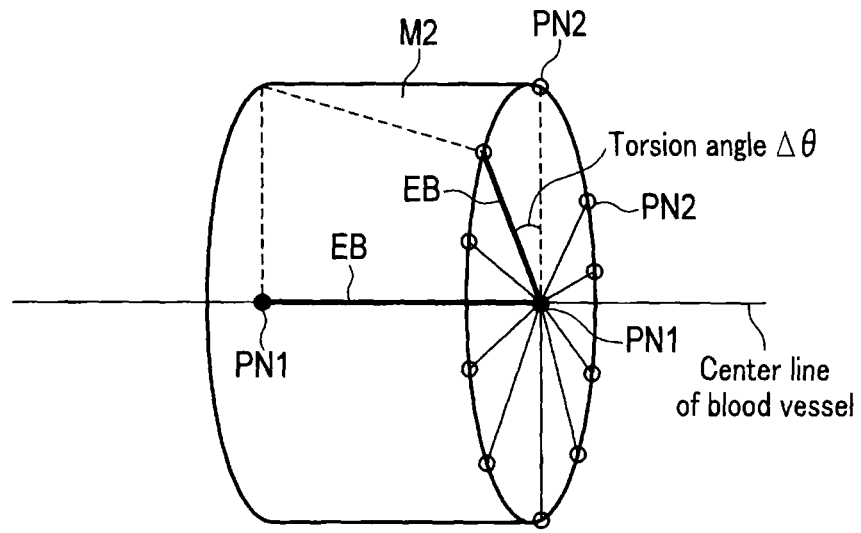
FIG. 10 is a figure for explaining allocation of a forcible displacement history to a shape model performed by the dynamical model structuring circuitry of FIG. 4.

In FIG. 10, the shape model M2 illustrates a portion of the dynamical model of the blood vessel and the blood, and FIG. 10 is a figure for explaining allocation of the forcible displacement history to the node in the dynamical model. FIG. 10 illustrates a portion of the shape model M2. However, although FIG. 10 shows a case where the center line is located in the M2, the center line may also be located outside of the M2. As shown in FIG. 10, multiple nodes PN (PN1, PN2) are set in the shape model M2. The node on the center line is referred to as PN1, and the nodes in the dynamical model indicating the blood vessel and the blood will be referred to as PN2. The shape model M2 is set for the dummy element surface, the blood vessel external wall, the blood vessel wall, the plaque region surface, the inside of the plaque region, or the blood region. The dynamical model structuring circuitry 55 allocates the forcible displacement to each node PN1 of the shape model M2, and more specifically, allocates the blood vessel shape change index for each time.

More specifically, the dynamical model structuring circuitry 55 connects the node PN1 and the node PN1, which regiondjacent to each other on the center line, with a beam element (or rigid element) EB. The dynamical model structuring circuitry 55 connects the node PN1 and another node PN2 included in a longitudinal cross section passing through the node PN1 with a beam element EB. The dynamical model structuring circuitry 55 allocates the constraint condition about the shape displacement direction of each blood vessel shape deformation index to the node PN1 and the beam element EB. In the region where the internal pressure of the material model and the intravascular lumen is identified, the forcible displacement includes the expansion and contraction of the blood vessel wall (or dummy element) surface in the center line direction, the twisting of the blood vessel wall (or dummy element) surface, and the bending deformation of the blood vessel wall (or dummy element) surface. For example, in the region where the internal pressure of the material model and the intravascular lumen is not identified, not only the forcible displacement in the center line direction and the time-series expansion and contraction (displacement) of the blood vessel wall in the circle regionlso allocated as the forcible displacement history. In a case where there is a protrusion on the intravascular lumen or in a case where the internal pressure such as a blood vessel branching portion affects deformation outside of the cross section in the center line direction, the forcible displacement history is not allocated to the region, and the forcible displacement history is allocated to only the peripheral portion of the region (for example, the surface node of the dummy element). The dynamical model structuring circuitry 55 allocates the time-series blood vessel shape deformation index to the node PN1 and the beam element EB as the forcible displacement history. In this manner, the expansion and contraction deformation, the twisting deformation, and the bending deformation about the entire blood vessel or the local portion thereof are expressed.

Figure 11:
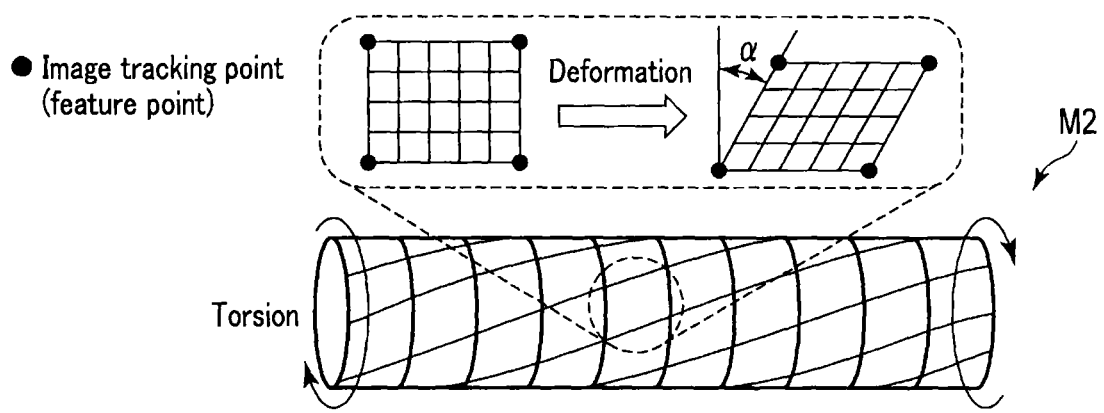
FIG. 11 is a figure illustrating another allocation method of a forcible displacement history to a shape model performed by the dynamical model structuring circuitry of FIG. 4, and illustrating an example of allocation of in a case where a blood vessel shape deformation index is twist.
Figure 12:
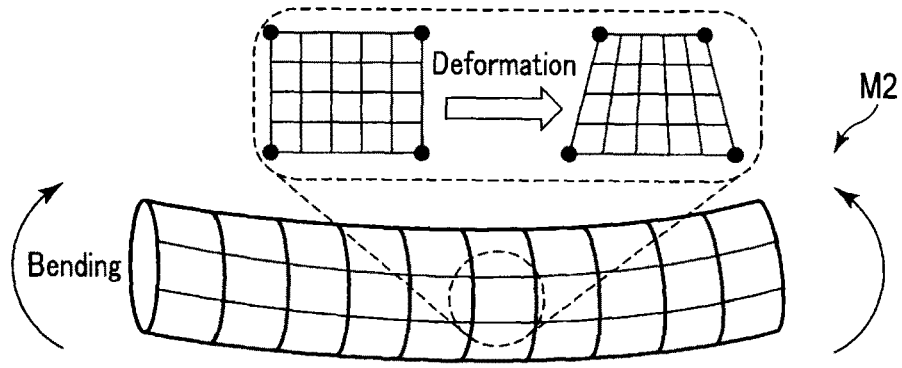
FIG. 12 is a figure illustrating another allocation method of a forcible displacement history to a shape model performed by the dynamical model structuring circuitry of FIG. 4, and illustrating an example of allocation of in a case where a blood vessel shape deformation index is bending.

It should be noted that the allocation target of the forcible displacement history is not limited to the node and the beam element of the center line. FIGS. 11 and 12 are figures illustrating another allocation method of the forcible displacement history to the shape model. FIG. 11 is an example of allocation in a case where the blood vessel shape deformation index is twisting. FIG. 12 is an example of allocation in a case where the blood vessel shape deformation index is bending. As shown in FIGS. 11 and 12, the dynamical model structuring circuitry 55 may directly allocate the forcible displacement history to the surface of the shape model or the node inside thereof. For example, in step S2, the image analysis/tracking processing circuitry 53 calculates blood vessel shape deformation index such as the expansion and contraction amount, the twisting amount, the bending amount, and the like about the feature point. The dynamical model structuring circuitry 55 directly allocates the calculated blood vessel shape deformation index to the nodes around the feature point by interpolation (interpolation and extrapolation).

The image processing circuitry 27 according to the present embodiment performs inverse analysis using the dynamical model temporarily structured in step S3, and statistically identifies the latent variable that is set in the dynamical model. The statistical identification processing is performed in step S6 explained later. Steps S4 and S5 are provided to calculate the blood vessel morphology index and the blood flow volume index used for the statistical identification processing.

When step 3 is performed, the system control circuitry 21 causes the image processing circuitry 27 to perform the blood vessel stress analysis processing (step S4). In step S4, the blood vessel stress analysis circuitry 57 of the image processing circuitry 27 performs the blood vessel stress analysis on the dynamical model of the current stage, and calculates prediction value of the time-series blood vessel morphology index. The blood vessel morphology index may be any of blood vessel morphology indexes explained above, and, for example, it is preferable to use the cross section shape index of the lumen region in the blood vessel center line direction and the cross section shape index of the blood vessel wall. More specifically, the cross section shape index of the lumen region is any one of the coordinate value of the attention-given pixel in the lumen region and the geometric structure parameter in the lumen region (the radius of the lumen region, the diameter of the lumen region, and the like). More specifically, the cross section shape index in the blood vessel wall region is any one of the coordinate value of the attention-given pixel in the blood vessel wall region and the geometric structure parameter in the blood vessel wall region (the radius of the blood vessel wall region, the diameter of the wall region, and the like). It should be noted that the prediction value means the calculation value of the blood vessel morphology index calculated by performing the blood vessel stress analysis on the dynamical model.

When step 3 is performed, the system control circuitry 21 causes the image processing circuitry 27 to perform the blood fluid analysis processing (step S5). In step S5, the blood fluid analysis circuitry 59 of the image processing circuitry 27 performs the blood fluid analysis to the temporarily structured dynamical model to calculate the prediction value of the time-series blood flow volume index. The blood flow volume index is the amount of blood flow or the flow rate. Alternatively, the blood flow volume index may be a spatial or temporal average value of the amount of blood flow or the flow rate. It should be noted that the prediction value means the calculation value of the blood fluid index calculated by performing the blood fluid analysis on the dynamical model.

When steps S4 and S5 are performed, the system control circuitry 21 causes the image processing circuitry 27 to perform the identification processing (step S6). In step S6, the statistical identification circuitry 61 of the image processing circuitry 27 statistically identifies the parameter of the latent variable of the dynamical model so that the prediction value of the blood vessel morphology index calculated in step S4 and the blood flow volume index calculated in step S5 match with the observation value of the blood vessel morphology index and the blood flow volume index collected in advance.

As shown in FIG. 4, the statistical identification circuitry 61 includes a first statistical identification circuitry 61-1 and a second statistical identification circuitry 61-2. The first statistical identification circuitry 61-1 statistically identifies the parameter of the latent variable so that the prediction value of the blood vessel morphology index is in conformity with the observation value of the blood vessel morphology index. The second statistical identification circuitry 61-2 statistically identifies the parameter of the latent variable so that the prediction value of the blood flow volume index is in conformity with the observation value of the blood flow volume index. Hereinafter, the first statistical identification circuitry 61-1 and the second statistical identification circuitry 61-2 will be explained in order.

More specifically, in step S6, the first statistical identification circuitry 61-1 sets the data distribution based on the prediction value and the observation value of the blood vessel morphology index calculated in step S4. The data distribution indicates, for example, a multivariate normal distribution function about an error of the prediction value and the observation value of the blood vessel morphology index. More specifically, the statistical identification processing circuitry 61-1 calculates the normal distribution function value of the error between the prediction value and the observation value for each node or each element in the dynamical model, and sets a product of each normal distribution function value as data distribution. The data distribution may be set individually for each time, or may be set collectively for multiple times. Subsequently, the first statistical identification circuitry 61-1 allocates prior distribution (prior probability distribution) to the latent variable of the dynamical model. More specifically, the prior distribution is allocated to each parameter related to material model, boundary condition, load condition, and uncertainty of the shape deformation index and the time-series morphology index. For example, the prior distribution related to the pressure value related to the intravascular lumen which is one of the parameters of the load condition is allocated. The range of the value that can be taken by the pressure value (expected range) can be limited empirically in advance. The first statistical identification circuitry 61-1 executes Monte Carlo simulation of the internal pressure value with limitation within the expected range, so that the probability distribution of the internal pressure value, i.e., the prior distribution, is calculated for each discretized region. When it is observed, as the prior distribution, that the pressure distribution in the center line direction is smooth, the pressure change over the elapse of the time is smooth, and there is no backward flow of bloodstream, then the dynamical model structuring circuitry 55 may set, as a prior distribution, a probability distribution where the inclination of the average pressure change in the center line direction is expressed mathematically by, for example, a multivariate normal distribution function. In accordance with the probability distribution limited into the expected range, the Monte Carlo simulation about the parameter of the load condition can be executed, and the sampling value of the load condition for setting in the dynamical model (latent variable) can be obtained. Subsequently, the first statistical identification circuitry 61-1 performs the statistical identification processing on the prior distribution and the data distribution for each latent variable, and calculates the posterior distribution (posterior probability distribution). The statistical identification processing includes, for example, hierarchical Bayesian model and Markov chain model. Then, the first statistical identification circuitry 61-1 identifies the parameter of each latent variable from the statistical value such as the modal value and the average value of the posterior distribution for each latent variable. For example, in the above example, the posterior distribution of the intravascular lumen pressure value is calculated, and the identification value of the intravascular lumen pressure value is calculated from the posterior distribution.

Figure 13:
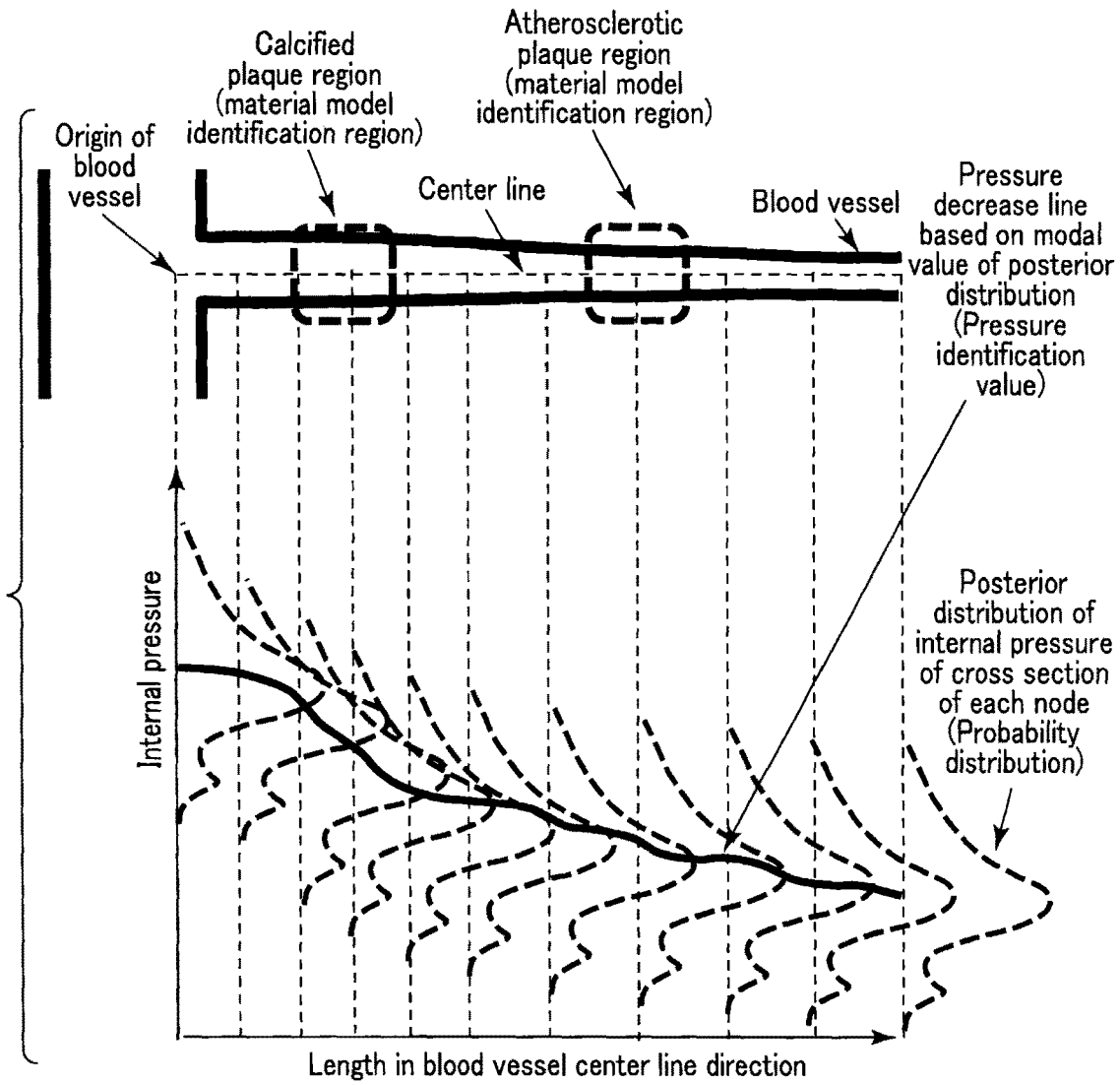
FIG. 13 is a figure for explaining posterior distribution calculation and identification of an average internal pressure of a load condition (an average pressure in a blood vessel) according to hierarchical Bayesian model and Markov chain Monte Carlo methods performed by the statistical identification circuitry of FIG. 4.

FIG. 13 is a figure for explaining identification of the average internal pressure and the posterior distribution calculation about the load condition based on hierarchical Bayesian model and Markov chain Monte Carlo method (the average pressure in the blood vessel). As shown in FIG. 13, the calcified plaque region and the atherosclerotic plaque region are considered to be set in the blood vessel extending from the blood vessel origin. The calcified plaque region is set in the material model identification region, and in the atherosclerotic plaque region, the material model identification region is set. The blood vessel internal pressure decreases along the blood vessel center line direction from the blood vessel origin. Multiple nodes are set along the blood vessel center line. In the longitudinal cross section (node cross section) including each node, the posterior distribution of the lumen internal pressure is calculated, and the modal value of the posterior distribution is identified.

For example, the blood vessel morphology index calculated in step S2 is used as the observation value of the blood vessel morphology index.

The processing performed by the second statistical identification circuitry 61-2 is the same as the processing performed by the first statistical identification circuitry 61-1 only in that the index used for calculation of the data distribution is different. More specifically, first, the second statistical identification circuitry 61-2 sets the data distribution based on the prediction value and the observation value of the blood flow volume index calculated in step S5. Subsequently, the second statistical identification circuitry 61-2 allocates the prior distribution to the latent variable of the dynamical model. For example, the prior distribution of the parameter of the material model about the blood vessel, the parameter of the material model about the blood, and the parameter of the material model about the plaque allocated. Examples of parameters of the material model include material model parameters such as parameters of an elastic modulus and viscosity of the constitutive equation of the blood. The probability distribution and the expected range of the parameter of the material model can be set empirically in advance. The second statistical identification circuitry 61-2 sets the probability distribution of the parameter of the material model for each discretized region, and more specifically, the second statistical identification circuitry 61-2 sets the prior distribution, and in accordance with the probability distribution limited into the expected range, the Monte Carlo simulation of the parameter of the material model can be executed, and the sampling value of the material model parameter for setting in the dynamical model (latent variable) can be obtained. Subsequently, the second statistical identification circuitry 61-2 calculates the posterior distribution by performing the statistical identification processing on the prior distribution and the data distribution for each latent variable, and identifies the parameter of each latent variable from the statistical value of the calculated posterior distribution. For example, in the above example, the posterior distribution of the parameter of the material model is calculated, and the identification value of the parameter of the material model is calculated from the posterior distribution.

Figure 14:
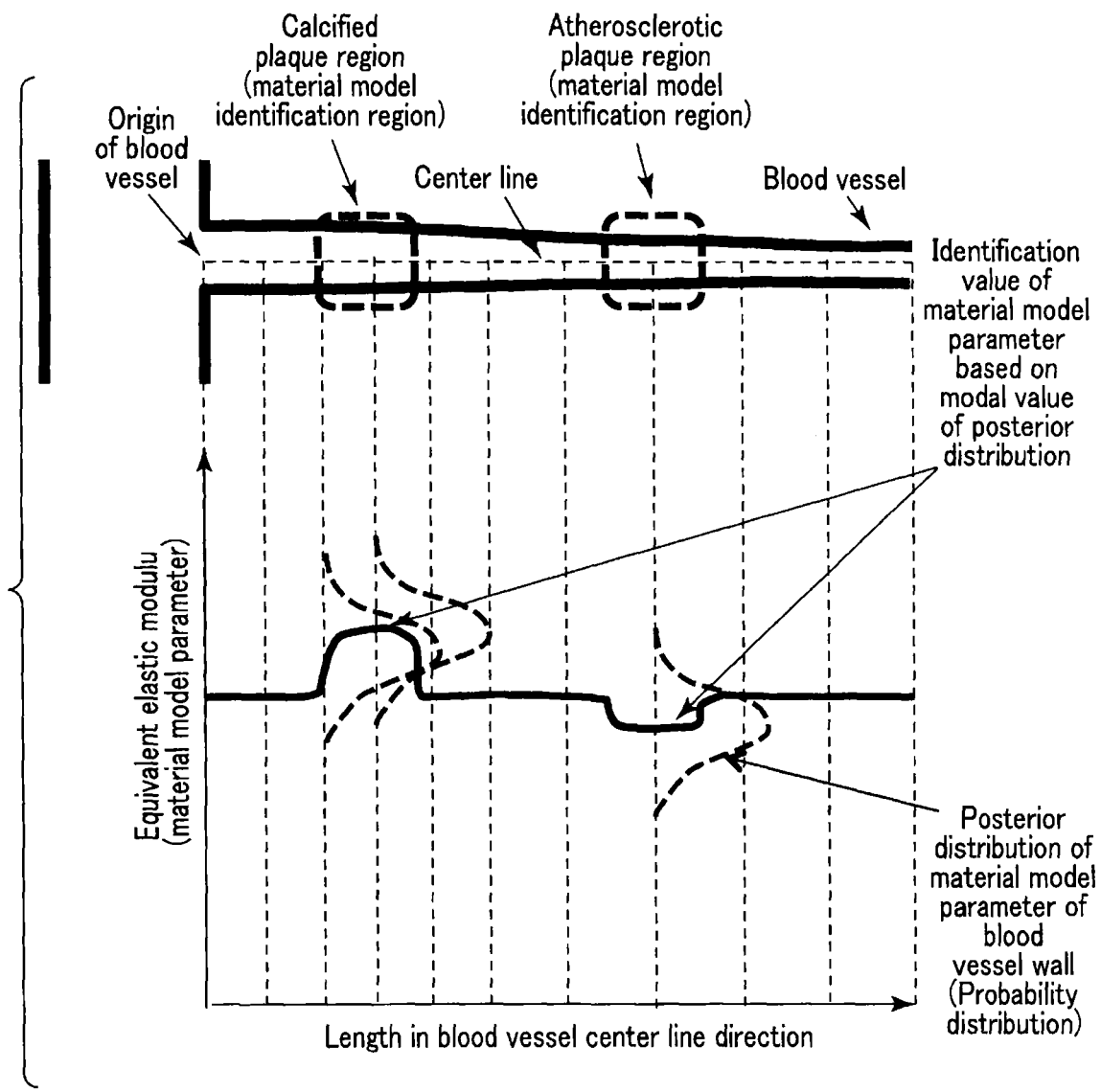
FIG. 14 is a figure for explaining identification of a material model parameter and a posterior distribution calculation about the material model parameter based on hierarchical Bayesian model and Markov chain Monte Carlo method (an equivalent elastic modulus of a blood vessel wall) performed with the statistical identification circuitry of FIG. 4.

FIG. 14 is a figure for explaining the identification of the material model parameter and the posterior distribution calculation about the material model parameter based on hierarchical Bayesian model and Markov chain Monte Carlo method (the equivalent elastic modulus of the blood vessel wall). As shown in FIG. 14, the blood vessel model is the same as FIG. 13. The posterior distribution of the parameter of the material model of the blood vessel wall (for example, the equivalent elastic modulus) is calculated by limiting into the material model identification region, and the modal value of the posterior distribution is identified.

It should be noted that the observation value of the blood flow volume index is assumed to be, for example, the amount of blood flow change flown to the pulmonary artery, and the observation value of the blood vessel morphology index can be used as the capacity change value (CFA) of the left ventricle measured by the image processing from the time-series CT image. The temporal change of the movement amount of the feature point is calculated by the image tracking of the contrast medium after the contrast medium is injected into the coronary artery, so that the flow rate and the amount of flow may be calculated. The density change amount of the contrast medium in the temporal particular region or the blood vessel center line direction is obtained, and the flow rate and the amount of flow may be calculated from the temporal rate of change of the density change and the value obtained by dividing the density change by the distance interval distance in the center line direction of each region. In the case of MRI, the image tracking of proton is used, and in a case of ultrasonic echo, the amount of flow is calculated by contrast echocardiography and the like.

When the coordinate value of each pixel of the analysis target region is assumed not to be the determined value, and more specifically, when there is uncertainty in the geometric structure of the analysis target region, the geometric structure may be included in the latent variable. In this case, the statistical identification circuitry 61 may set, as the prior distribution, the probability distribution of normal distribution and the like expressing the change within a predetermined range in the center line direction of the coordinate value of each node or the change within a predetermined range of the diameter in the analysis target region. In this case, constraints, i.e., the shape of the analysis target region is smooth, and the order of the nodes in the center line is unchanging, may be set as the prior distribution. In accordance with the probability distribution limited to the expected range, Monte Carlo simulation about the parameter of the geometric structure can be executed, and the sampling value of the uncertainty parameter of the geometric structure for setting to the dynamical model (latent variable) can be obtained.

In each step S6, both of the statistical identification processing with the first statistical identification circuitry 61-1 and the statistical identification processing with the second statistical identification circuitry 61-2 may not be performed. More specifically, in step S6, any one of the statistical identification processing with the first statistical identification circuitry 61-1 and the statistical identification processing with the second statistical identification circuitry 61-2 may be performed.

In the above example, the first statistical identification circuitry 61-1 statistically identifies the parameter of the latent variable so that the prediction value of the blood vessel morphology index is in conformity with the observation value of the blood vessel morphology index, and the second statistical identification circuitry 61-2 statistically identifies the parameter of the latent variable so that the prediction value of the blood flow volume index is in conformity with the observation value of the blood flow volume index. However, the statistical identification circuitry 61 may statistically identify the parameter of the latent variable based on the structure-fluid interaction analysis so that the prediction value of the blood vessel morphology index and the prediction value of the blood flow volume index are in conformity with the observation value of the blood vessel morphology index and the observation value of the blood flow volume index. Further details of the statistical identification processing with the statistical identification circuitry 61 will be explained later.

When step S6 is performed, the dynamical model structuring circuitry 55 of the image processing circuitry 27 sets the parameter of the latent variable calculated in step S6 to the dynamical model.

Then, the system control circuitry 21 determines whether the identification termination condition is satisfied or not (step S7). When the identification termination condition is determined not to be satisfied in step S7 (step S7: NO), the system control circuitry 21 repeats steps S4, S5, S6, and S7. In this case the identification termination condition is expressed by whether the index for determining the identification termination (hereinafter referred to as an identification termination index) attains the defined value. Examples of identification termination indexes include a difference value between the prediction value and the observation value of the blood vessel morphology index. In this case, when this difference value is more than an already-determined value, the system control circuitry 21 determines that the identification termination condition is not satisfied, and when the difference value is less than the already-determined value, the system control circuitry 21 determines that the identification termination condition is satisfied. For example, the identification termination index may be the number of sampling points of the Monte Carlo method. In this case, when the number of sampling points is less than the already-determined value, the system control circuitry 21 determines that the identification termination condition is not satisfied, and when the number of sampling points is more than the already-determined value, the system control circuitry 21 determines that the identification termination condition is satisfied. When the identification termination condition is determined to be satisfied, the dynamical model structuring circuitry 55 sets the latest dynamical model at that point in time to the ultimate dynamical model.

When the ultimate dynamical model is structured, the dynamical model structuring circuitry 55 calculates the observation value of the blood vessel shape deformation index, the parameter of the load condition of the ultimate dynamical model, and the model related to the parameter of the material model (hereinafter referred to as a related model). The related model is stored to the storage 33. The related model may be stored in association with patient information, inspection information, and the like for, e.g., the ease of the searching. It should be noted that the observation values of the blood vessel morphology index and the blood flow volume index, the parameter of the load condition of the ultimate dynamical model, and the parameter of the material model may not be necessarily associated in the mode of the model, and for example, the observation values of the blood vessel morphology index and the blood flow volume index, the parameter of the load condition of the ultimate dynamical model, and the parameter of the material model may be a table or a database.

Steps S4, S5, S6, and S7 explained above may be repeated according to the same identification method, or may be repeated according to different identification methods. When steps S4, S5, S6, and S7 are repeated in accordance with different identification methods, for example, first, a simplified dynamical model may be used to temporarily identify the latent variable, and subsequently, a continuum dynamical model may be used to accurately identify the latent variable. As described above, the statistical identification processing is performed in two steps in accordance with different schemes, and the parameter of the latent variable can be converged in a short time. A method using the simplified dynamical model includes an expression of a material dynamics of a thick cylinder of the internal pressure and the external pressure. The method using the simplified dynamical model may use an expression of Hagen-Poiseuille flow and modified Bernoulli. A method using a continuum dynamical model includes FEM structural fluid analysis. The details of the identification method using the simplified dynamical model and the identification method using the continuum dynamical model will be explained later.

When the identification termination condition is determined to be satisfied in step S7 (step S7: YES), the system control circuitry 21 may cause the image analysis/tracking processing circuitry 53 to perform amending processing (step S8). In step S8, the image analysis/tracking processing circuitry 53 may amend the shape of the blood vessel region included in the time-series medical image so that the structural fluid analysis result carried out based on the latent variable obtained by the inverse analysis according to the statistical identification method (the prediction values of the mechanics index and the prediction value of the blood fluid index) are in conformity with the observation values (the observation value of the mechanics index and the observation value of the blood fluid index). The display 31 displays a diagnosis result based on the amended time-series medical image. Therefore, the blood vessel analysis apparatus 50 can display the diagnosis result in view of the ultimate dynamical model. Alternatively, the display 31 may display, on a screen, a blood vessel portion/region in which the identification with the inverse analysis and the observation result with the structural fluid analysis are not in conformity. For example, when the image of a cardiac phase in which the motion of the behavior of the blood vessel is fast often blurred, and there is a portion and an region where the error is large in the blood vessel shape observed with the image analysis based on the medical image. Relatively, the medical image data in the cardiac phase in which the behavior of the blood vessel is stable involves less noise. Based on the blood vessel shape data of which error distribution is small, the blood vessel shape in the cardiac phase where the error is large can be correctly interpolated by using the dynamical model. With regard to the blood vessel portion and the region where the error is large, the correctly interpolated shape as well as the variation distribution from the original data can be displayed. Therefore, the stability of the blood vessel shape display can be ensured, and the user can recognize the uncertainty of the shape.

When step S8 is performed, the system control circuitry 21 causes the image processing circuitry 27 to perform the blood vessel stress analysis processing (step S9). In step S9, the blood vessel stress analysis circuitry 57 of the image processing circuitry 27 performs the blood vessel stress analysis on the ultimate dynamical model, and calculates the space distribution of the prediction value of the time-series mechanics index. More specifically, the prediction value of the mechanics index for each discretized region is calculated.

When step S8 is performed, the system control circuitry 21 causes the image processing circuitry 27 to perform the blood fluid analysis processing (step S10). The blood fluid analysis circuitry 59 of the image processing circuitry 27 in step S10 performs the blood fluid analysis on the dynamical model temporarily structured, and calculates the space distribution of the prediction value of the time-series blood flow volume index. More specifically, the prediction value of the blood flow volume index for each discretized region is calculated.

It should be noted that the FFR may be calculated as the mechanics index or the blood flow volume index.

When steps S9 and S10 are performed, the system control circuitry 21 causes the display 31 to perform the display processing (step S11). In step S11, the display 31 displays the prediction value of the time-series mechanics index calculated in step S9 and the prediction value of the time-series blood flow volume index calculated in step S10. For example, the display 31 displays the time-series mechanics index or the time-series blood vessel flow volume index in a motion picture manner in which the time-series dynamical model is in a color according to the prediction value. Therefore, the display 31 holds a color table indicating a relationship between various kinds of prediction values and color values (for example, RGB). The display 31 uses a color table to identify the color value according to the prediction value, and displays the discretized region corresponding to the prediction value in a color according to the color value identified.

FIG. 15 is a figure illustrating an example of display of a space distribution of an internal pressure which is one of mechanics indexes. As shown in FIG. 15, the display 31 displays each discretized region constituting the dynamical model in a motion picture manner in a color according to the internal pressure value about the discretized region. When the user observes the dynamical model, the user can find, based on the color, the mechanics index changing over time or space.

Figure 16:
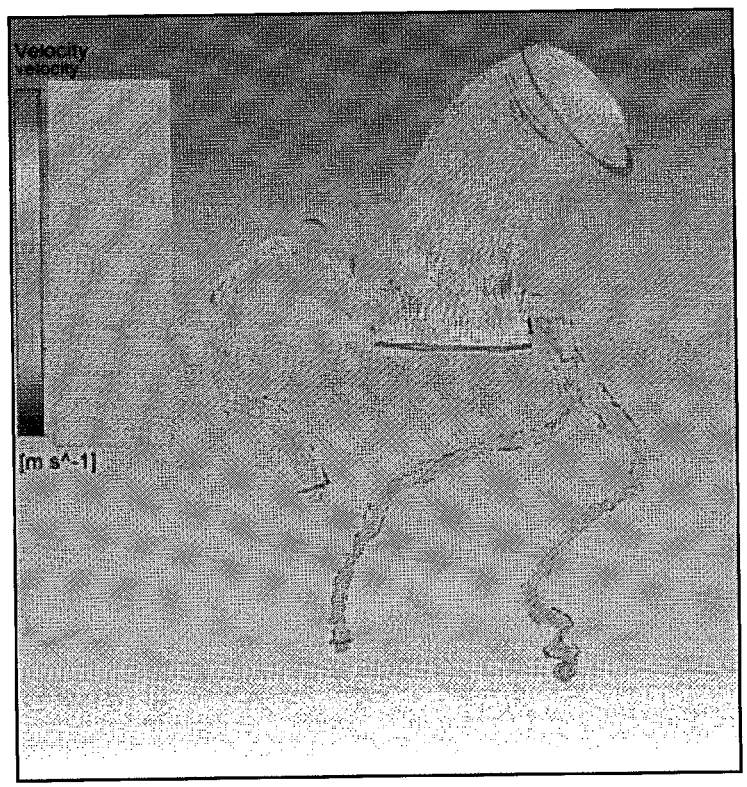
FIG. 16 is a figure illustrating an example of display of a space distribution of a flow rate value which is one of blood flow volume indexes performed with the display of FIG. 1.

FIG. 16 is a figure illustrating an example of display of a space distribution of a flow rate value which is one of blood flow volume indexes. As shown in FIG. 16, the display 31 displays each discretized region constituting the dynamical model in a motion picture manner in a color according to the flow rate value about the discretized region. When the user observes the dynamical model, the user can find, based on the color, the blood flow volume index changing over time or space.

For example, when the inside of the blood vessel is completely stenosed, the internal pressure of the stenosed portion is smaller than the internal pressure of the non-stenosed portion. When the internal pressure is designated as the mechanics index, the user can determine presence or absence of stenosis based on the local difference in the color on the dynamical model. The amount of flow of the stenosed portion is less than the amount of flow of the non-stenosed portion. When the amount of flow is designated as the blood flow volume index, the user can determine presence/absence of stenosis based on a local difference in the color on the dynamical model.

The blood vessel stress analysis circuitry 57 may calculate the space distribution of the hardness value as the mechanics index based on the identification result of the identification result of the material model parameter of the plaque region. In this case, the display 31 may also display the space distribution of the hardness value about the plaque region on the dynamical model. The display 31 displays the internal pressure distribution around the plaque region, the stress distribution, and the distortion distribution. The user can use these displays for estimating the property and the ease of rupture of the plaque.

The prediction values of the mechanics index and the blood flow volume index are not limited to the method for expressing with a color in the discretized region of the dynamical model. For example, as shown in FIG. 17, FIG. 18, and FIG. 19, the prediction values of the mechanics index and the blood flow volume index may be displayed in a graph. FIG. 17 is a graph related to the blood pressure of the left coronary artery origin. The vertical axis of the graph of FIG. 17 is defined as the normalized blood pressure, and the horizontal axis is defined as a cardiac phase [%]. FIG. 18 is a graph related to the blood pressure around the branch point of LCX and LDA. The vertical axis of the graph of FIG. 18 is defined as the normalized blood pressure, and the horizontal axis is defined as a cardiac phase [%]. FIG. 19 is a graph related to the blood pressure change in the center line direction. The vertical axis of the graph of FIG. 19 is defined as the blood pressure ratio, and the horizontal axis is defined as a distance [mm] from the pulmonary artery. The display 31 displays the prediction values of the mechanics index and the blood flow volume index in a graph, so that the user can easily find these values.

When step S11 is performed, the structural fluid analysis processing is terminated.

In FIG. 10, the forcible displacement history is set for the center line circuitry and the external wall circuitry of the shape model, but the setting portion of the forcible displacement history is not limited thereto. For example, the forcible displacement history may be set in the blood vessel wall region between the center line circuitry and the external wall circuitry.

It should be noted that the allocation target of the constraint condition of the forcible displacement history may be divided according to whether the boundary condition and the material model are identified or not. FIGS. 20A and 20B are figures illustrating another example of allocation of forcible displacement history, and illustrates a cross section of the shape model. For example, when the boundary condition and the material model are identified as shown in FIG. 20A, the forcible displacement history is allocated only to the node PN2 on the external wall circuitry OW of the shape model, and the forcible displacement history is allocated to the node PN3 of the blood vessel wall region RV. When the boundary condition and the material model are identified as shown in FIG. 20B, the forcible displacement history is preferably allocated to both of the node PN2 of the external wall circuitry of the shape model and the node PN3 of the blood vessel wall region RV. In this case, the forcible displacement history is allocated to the node PN1 on the center line. The node PN1 and the node PN2 of the external wall circuitry OW may be connected with the beam element EB, and the forcible displacement history may be allocated to the nodes PN2 and PN3 on the beam element EB. At this occasion, the contraction and the expansion in the circle are expressed as the expansion and contraction displacement of the beam element EB. The forcible displacement history may not be allocated to the intravascular lumen region RI.

FIG. 21 is a figure illustrating another example of allocation of forcible displacement history, and illustrates a cross section of the shape model including the dummy element RD of the perivascular tissue. As shown in FIG. 21, the dummy element RD is set outside of the blood vessel wall region RN. When the shape model includes the dummy element RD, the node PN4 is set to not only the blood vessel wall region RN but also the dummy element RD. The forcible displacement history is also allocated to the node PN4. When the boundary condition and the material model are identified, the dynamical model structuring circuitry 55 allocates the forcible displacement history to the node PN 3 included in the blood vessel wall region RV, and when the boundary condition and the material model are not identified, the dynamical model structuring circuitry 55 may not allocate the forcible displacement history. When the forcible displacement history is allocated to the node PN3, the material model is identified in view of not only the shape index of the lumen region RI but also the shape index of the blood vessel wall region RV.

FIG. 22 is a figure illustrating another example of allocation of forcible displacement history, and illustrates a cross section of the shape model including the plaque region RP. As shown in FIG. 22, the plaque region RP is included in the blood vessel wall region RV. The plaque region RP is set in the material model identification region. For the plaque region RP, the material model is identified in view of the lumen shape index, the blood vessel wall shape index, and the plaque index. As described above, for example, the plaque index is data about the property of the plaque obtained by the tissue property diagnosis with the ultrasonic diagnosis apparatus. The dynamical model structuring circuitry 55 divides the plaque region into multiple partial regions in accordance with the property, and sets the material model identification region individually for multiple partial regions. In each partial region, the parameter range according to the property of the partial region is preferably set in advance. With the statistical identification processing explained above, the material model parameter for each partial region is identified by the statistical identification circuitry 61. Then, in step S10, the display 31 displays the index about the material characteristics of the blood vessel as the mechanics index, so that the user can accurately and easily find the property of the plaque.

Subsequently, the material model which is one of the latent variables will be explained in details. The superelasticity model and the like can be applied as the material model of the blood vessel in view of elasticity model, superelasticity model, anisotropic superelasticity model, and viscosity characteristics. For example, a mathematical model called Y. C. Fun and a mathematical model called Holzapfel-Gasser constitutive equation can be applied as anisotropic superelasticity model. The distortion energy per circuitry reference cubic volume is expressed by the following expression (1). The first term of the expression (1) represents the energy of shearing deformation of an isotropic basic material not including collagen, and the second term represents the energy of cubic volume deformation of an isotropic basic material not including collagen, and the third term represents contribution of each group of a collagen fiber (in view of dispersion of a fiber direction).

$$U = C_{10}(\bar{I}_1 - 3) + \frac{1}{D}\left(\frac{(J^{el})^2 - 1}{2} - \ln J^{el}\right) + \frac{k_1}{2k_2}\sum_{\alpha=1}^{N}\left\{\exp[k_2(\bar{E}_\alpha)^2] - 1\right\} \quad (1)$$

Figure 23A:
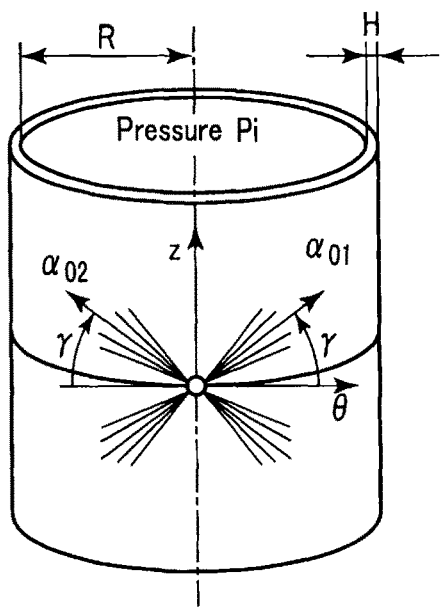
FIGS. 23A to 23C is a figure illustrating deformation of the fiber group according to the present embodiment.
Figure 23B:
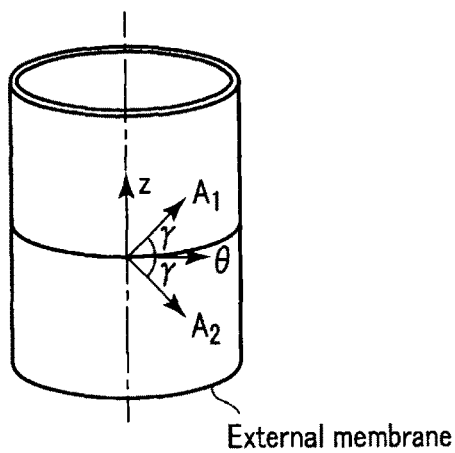
Figure 23C:
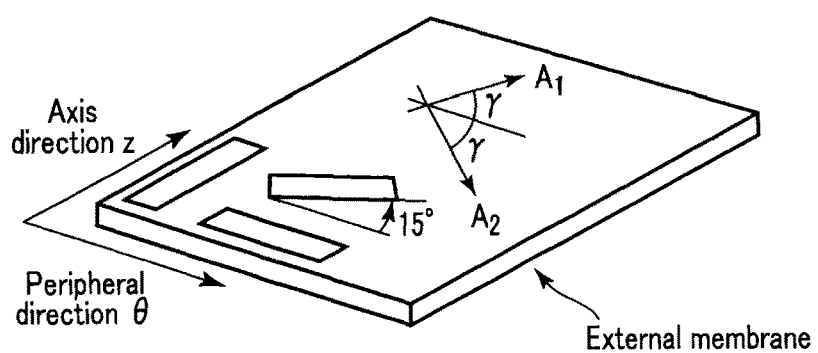

FIGS. 23A to 23C are figures illustrating deformation of the fiber group. As shown in FIGS. 23A to 23C, the outer membrane on the cylindrical shape is assumed. The deformation of the fiber group in the average direction A in the surface defined by the center line direction z and the peripheral direction θ is expressed by the following expression (2).

$$\bar{E}_\alpha{}^{def} = \kappa(\bar{I}_1 - 3) + (1 - 3\kappa)(\bar{I}_{4(\alpha\alpha)} - 1) \quad (2)$$

The parameter of the material model in the expressions (1) and (2) include a material parameter and a fiber dispersion parameter as shown in table 1 shown below. C10, D, K1, K2, and the like are used as material parameters, and Kappa and γ and the like are used as fiber dispersion parameters. The default values and the constraint conditions of each parameter regions shown in table 1.

TABLE 1

|  | Parameter | Unit | Default value | Constraint condition |
| --- | --- | --- | --- | --- |
| Material parameter | C10 | [MPa] | 7.64E−03 | — |
|  | D | — | 0 | — |
|  | k1 | [MPa] | 0.9966 | — |
|  | k2 | — | 524.6 | — |
| Fiber dispersion Parameter | Kappa | — | 0.226 | 0 < Kappa < 0.33 |
|  | γ | [°] | 49.98 | 45 < γ < 90 |

Casson constitutive equation as shown in the expression (3) and HB constitutive equation as shown in the expression (4) below are preferable as the material model of the blood.

$$\sqrt{\tau} = \sqrt{\tau_0} + \sqrt{\mu_\infty}\sqrt{\dot{\gamma}} \quad (3)$$

$$\mu = k\dot{\gamma}^{n-1} + \tau_0/\dot{\gamma} \quad (4)$$

Note that τ shows shearing stress, $\tau_0$ shows yield stress, μ shows viscosity coefficient, and γ shows shearing distortion speed The parameters of the material models are identified in the statistical identification processing using the blood vessel morphology index and the blood fluid index by the statistical identification circuitry 61 in step S6 explained above.

Subsequently, the details of the statistical identification processing performed by the statistical identification circuitry 61 will be explained.

The observation variables such as the blood vessel morphology index and the blood flow volume index measured from the time-series medical image involve uncertainty. The statistical identification circuitry 61 makes use of the statistical scheme based on hierarchical Bayesian model and Markov chain Monte Carlo method as a statistical identification method of latent variable under a situation where such uncertainty exists.

As described above, in step S6, the statistical identification circuitry 61 sets data distribution based on the prediction value and the observation value of the blood vessel morphology index or the blood flow volume index calculated in step S4. For example, the data distribution indicates a multivariate normal distribution function about an error of the prediction value and the observation value of the blood vessel morphology index or the blood flow volume index. The data distribution may be set individually for each time, or may be set collectively for multiple times. Subsequently, the statistical identification circuitry 61 allocates the prior distribution to the latent variable and the forcible displacement of the shape model. The prior distribution indicates the probability distribution of the value that may occur. Subsequently, the statistical identification circuitry 61 executes the parameter survey of the numerical simulation about the latent variable, and structures a model expressing a relationship between the latent variable and the blood vessel morphology index or the blood flow volume index. For example, a relationship of the material model parameter, the internal pressure distribution parameter, and the blood vessel morphology index or the blood flow volume index is defined in a model. A relationship of the blood vessel morphology index or the blood flow volume index and the latent variable may not be in a form of a model but may be defined in a database or a table. These models, databases, or tables are stored in the storage 33. By using the models, databases, or tables, the statistical identification circuitry 61 calculates the probability distribution of the blood vessel morphology index or the blood flow volume index from the prior distribution. The statistical identification circuitry 61 statistically identifies the latent variable from the posterior distribution obtained from hierarchical Bayesian model and Markov chain Monte Carlo method.

More specifically, this identification problem is a fault setting problem of not satisfying the following three conditions. The three conditions include (1) an existence of solution is ensured, (2) the fault setting problem is uniquely determined, and (3) the solution changes continuously for data, and the solution is stable with respect to the measurement error. The fault setting problem can be easily treated when it is understood within a frame including the normalization theory and the expansion thereof. An ordinary normalization theory is insufficient for solving the fault setting problem. In order to solve the fault setting problem, it is necessary to have a methodology for detecting discontinuity of internal state and using the detected discontinuity for the estimation of the internal state. With regard to this point, the Markov probability field theory is effective in the statistical identification processing according to the present embodiment.

Under an environment where there is uncertainty in the blood vessel morphology index and the blood flow volume index, the statistical identification circuitry 61 identifies the probability distribution parameter of the latent variable under an appropriate constraint condition. In order to determine an appropriate constraint condition, it is necessary to know the property of the solution in advance. The statistical identification circuitry 61 generates a database about a constraint condition of the solution space based on the simulation and the observation value. The statistical identification circuitry 61 uses the generated database to execute statistical identification processing based on Markov probability field theory and hierarchical Bayesian model for the super multi-degree freedom large-scale problem. In the setting of the prior distribution which is the constraint condition, the probability distribution of the parameter about these factors based on many numerical experiment results is configured in a parallel and individual manner. The statistical identification circuitry 61 identifies the parameter of the latent variable by uniting multiple probability distributions and interpolating defects of data. For this processing, the statistical identification circuitry 61 performs estimation according to hierarchical Bayesian method based on a model using Markov probability field theory. This is a mechanism capable of estimating the amount of flow distribution and the pressure at any given load condition and boundary condition based on an identified intermediate variable from actually measured result of deformation of the structure of the analysis target.

The identification problem of the material model, the boundary condition, and the load condition in the structural fluid analysis of coronary artery is identified as non-linear inverse analysis, and in many cases, uniqueness and stability of solution are not guaranteed. A range of the blood pressure that can occur in reality and the material characteristics of living tissue can be expected as a priori information, and therefore, they can be set as the probability distribution of the prior distribution. In addition, the pressure and the displacement can also be expected to be smooth temporally in terms of space, and therefore, this information can also be set as the probability distribution of the prior distribution as a priori information. Alternatively, when it is possible to consider the fact that a backward flow is occurring in the flow of the blood, it may also be possible to use, as a constraint condition, a fact that the overall inclination of the pressure distribution in the blood vessel center line direction is negative (there is decrease in the pressure). A square error distribution of the prediction value of the blood vessel shape deformation index based on the dynamical model and the observation value of the blood vessel shape deformation index based on the time-series CT image can be set as the data distribution to the load condition (internal pressure distribution and the like), the boundary condition, and the material model. A square error distribution about the average amount of flow that can be observed may also be added as a data distribution. The posterior distribution can be calculated by using Monte Carlo method and hierarchical Bayesian model based on the data distribution and these prior distributions. The identification value of the parameter of the latent variable can be obtained from the dispersion and the occurrence probability of the posterior distribution. When the occurrence probability is higher and the dispersion is smaller, the identification value can be said to have a high reliability degree. Even in a case where the posterior distribution is multimodal distribution, an identification value of which dispersion is small may be selected from among multiple identification values. Alternatively, when there may be multiple identification values, the structural fluid analysis is carried out with each identification condition, and each possibility is recognized, and the identification value and the analysis result can be used as guide information for diagnosis and prevention. Since the time-series CT image also includes error, the blood vessel morphology index about each node of the dynamical model also includes error. For this reason, each blood vessel morphology index is treated as, for example, the probability variable of the normal distribution in which the prediction value of the blood vessel morphology index measured from the time-series CT image is the average value, and the constraint for maintaining the order in terms of space of the position is included, and thus the prior distribution may be set. In the identification of the parameter of the latent variable, there may be no uniqueness and there may be multiple candidates. In this case, the robustness (stability) of a candidate of each identification value is determined by checking the fluctuation range of the sample set of the identification value of the latent variable for the sampling point of a random number according to uncertainty of the blood vessel morphology index measured from the time-series CT image. The ultimate identification value may be determined based on the robustness of the candidate of each identification value.

Subsequently, the details of the dynamical model will be explained. As described above, the dynamical model structuring circuitry 55 can structure a dynamical model of a type different according to the type of the dynamical model. When an FEM based on continuum mechanics is used, the dynamical model structuring circuitry 55 structures both of the shape model for stress analysis of blood vessel wall (FEM model) and the shape model for blood fluid analysis (FEM model).

When a simplified identification method is used based on the material dynamics, a relationship of pressure, elastic modulus, and displacement is derived from an expression of a thick cylinder receiving the internal pressure of the material dynamics. In this case, a thick cylinder approximation of each of multiple discretized regions arranged in the center line direction is used as the shape model. More specifically, the dynamical model structuring circuitry 55 identifies the cross section center, the blood vessel wall surface shape, and the intravascular lumen shape in the cross section passing the nodes arranged in a discrete manner on the center line. Subsequently, the dynamical model structuring circuitry 55 calculates an average region size, a lumen average radius, and an average wall thickness based on the intravascular lumen shape and the blood vessel wall surface shape. Then, the dynamical model structuring circuitry 55 structures the shape model by performing thick cylinder approximation in the blood vessel region of each discretized region based on the average region size, the lumen average radius, and the average wall thickness.

In a case where a simplified identification method based on flow dynamics is used, an expression of modified Bernoulli of fluid dynamics or an expression of Hagen-Poiseuille Flow (Hagen-Poiseuille flow) are used in order to approximately derive the average pressure and the average amount of flow of the bloodstream. In this case, a shape model is structured in order to approximately derive a relationship of the amount and the blood pressure difference of flow of each of multiple discretized regions. In this case, the blood pressure difference is a pressure difference of the pressure at the entrance and the pressure at the exit, and the amount of flow means the entrance amount of flow (or flow rate) and the exit amount of flow (or flow rate) per circuitry time. However, the dynamical model structuring circuitry 55 may associate the movement vector of each node and the rotation displacement of a node adjacent to the node in question at each time based on the torsion angle and the expansion and contraction distance in the center line direction calculated in step S2.

Subsequently, the structural fluid analysis using the continuum dynamical model will be explained.

Kinematics of the blood vessel and the blood (substances constituting the blood vessel and the blood) is irrelevant to the force causing the motion. The basic concept of kinematics about blood vessel and blood is obtained by making an intuitive concept about a set of a position, a time, an object, a motion, and a substance that can be deformed into an abstract mathematical term. Basic kinematics tensor dominating local analysis of deformation and motion about blood vessel and blood region deformation inclination tensor F and a speed inclination tensor L. The deformation inclination tensor F defines the change in the size and the shape that occur in the substance element of blood vessel and blood making motion. The deformation inclination tensor F is expressed by a product of a rotation tensor (proper orthogonal tensor) R and stretching tensors (positive value symmetrical tensors) U, V. The stretching tensors U, V are derived by, first, applying stretch in a direction defined by the normal orthogonal vector R in the basic mode and subsequently applying rigid body rotation given by the normal orthogonal vector R. The step of applying stretch and the step of applying rigid body rotation may be performed in the opposite order. The speed inclination tensor L does not depend on the reference mode and depends only on the current mode. The speed inclination tensor L defines the speed at which there is a change in the size and the shape that occurs in the substance element of blood vessel and blood making motion. The speed inclination tensor L can be divided into the distortion speed tensor D (symmetrical tensor) and the spin tensor (antisymmetrical tensor). The distortion speed tensor D expresses the rate of change of the stretch when the object exactly passes the current mode. The spin tensor represents the rate of change of the rotation when the object exactly passes the current mode. A displacement constraint condition (including temporal change) is allocated to the speed inclination tensor and the deformation inclination tensor about a portion of an external surface node (or integration point) of a dynamical model of the blood vessel. The parameter of the material model, the load condition (the surface force vector of the lumen of the dynamical model), and the boundary condition (the force vector of the blood vessel boundary) are identified so that the prediction value of the lumen node (or integration point) of the dynamical model (the deformation the inclination tensor, the speed inclination tensor, or these function values (which may be, for example, displacement and region size)) and the observation value (the deformation inclination tensor, the speed inclination tensor, or the function thereof obtained from observation data) are in conformity. In this case, the initial state of the stress of the blood vessel internal may be temporarily determined in advance or identified.

The dynamical model based on the continuum mechanics is based on an equation representing equilibrium of mass, kinematics, motion amount, angle motion amount, and energy of blood vessel and blood in motion. The concept of mass, force, energy, and internal energy is a basic. The equilibrium law means that the time total differentiation of the motion amount becomes equal to a summation of the object force and the contact force, and the time total differentiation of the angle motion amount becomes equal to a summation of the object torque and the contact torque, and the temporal change of the motion energy and the internal energy becomes equal to a summation of the heat supply and the heat flux per circuitry time and the power (mechanics energy). Equations of fields such as deformation inclination tensor, speed inclination tensor, and stress tensor are derived from equilibrium law, constitutive equation, and jump condition, and the dynamical model of the blood vessel and the blood can be described. The distortion field of the blood vessel and the blood satisfies the conformity condition. In this case, the constitutive equation gives a relationship of a set of ten scalar equations made up with density, internal energy, speed vector, stress tensor, heat flux vector, and temperature. 17 scalar fields of equilibrium equations of field are given, and more specifically eight scalar relationships with the equilibrium of the field are given from among density, internal energy, speed vector, stress tensor, and heat flux vector, and a relationship of remaining unknown amount also including the temperature is given. However, the object force b and the heat source r already known. The parameters of equations giving the scalar fields are material model parameters.

The dynamical model based on the continuum mechanics can calculate approximation solutions of fields such as displacement vector, stress tensor, distortion tensor, and speed vector according to numerical analysis method based on finite element method or boundary element method based on the boundary condition, the load condition, and the material model given.

In the structure-fluid interaction analysis, the method of solving the equation of the structure and the fluid may be either monolithic method or partitioned method. The interaction on the boundary surface between the structure and the fluid may be either weak interaction or strong interaction. In the fluid analysis, movement boundary may be treated according to a boundary surface tracking-type scheme such as ALE method, or boundary surface capturing-type scheme such as Immersed Boundary method, Immersed Finite Element Method, Fictitious Domain Method, and the like.

Subsequently, an expression of material dynamics of a thick cylinder receiving the internal pressure and the external pressure and an expression of Hagen-Poiseuille flow and modified Bernoulli will be explained in details as an example of simplified dynamical model.

Figure 24:
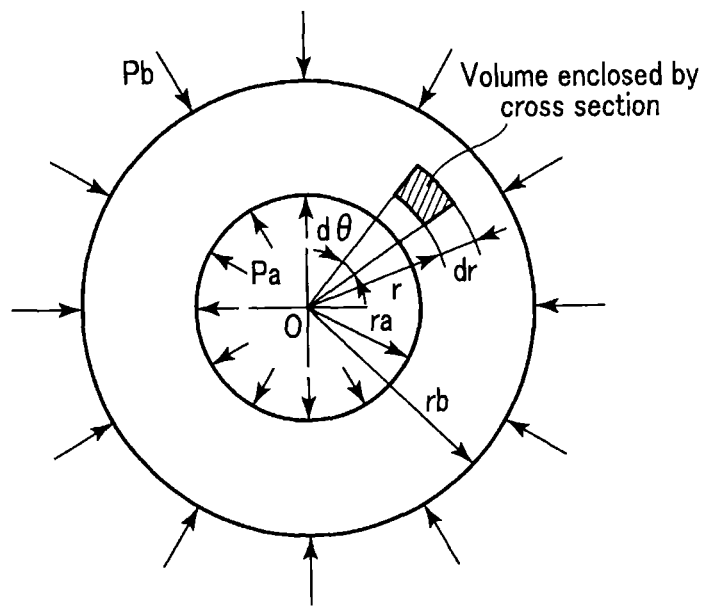
FIG. 24 is a figure illustrating a longitudinal cross section of a dynamical model of a thick thickness cylinder according to the present embodiment.
Figure 25:
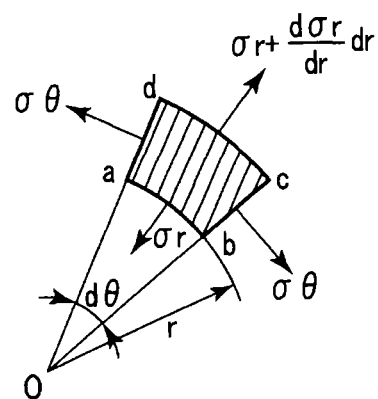
FIG. 25 is an enlarged view illustrating a micro sector element of FIGS. 20A and 20B.

First, an expression of material dynamics of a thick cylinder will be explained with reference to FIG. 24 and FIG. 25. FIG. 24 is a figure illustrating a longitudinal cross section of a dynamical model of a thick thickness cylinder, and FIG. 25 is an enlarged view illustrating a micro sector element of FIG. 24. An expression of stress, distortion, displacement, and the like in a case where an internal pressure $p_a$ and an external pressure $p_b$ are exerted on thick cylinders having an internal radius $r_a$ and an outside radius $r_b$ will be explained. E and ν denotes a material model parameter. E denotes an elastic modulus, and ν denotes a Poisson ratio. In the thick cylinder, it is necessary to also consider the radius stress $\sigma_r$, and the circle distribution of the circumference stress $\sigma_\theta$. In the explanation below, the distortion $\varepsilon_z$ in the axis direction is assumed to be uniform in terms of the position and the direction in the cross section. A case where the cylinder cross section is axis symmetrical will be explained, but it may be any given shape. In a case where the cylinder cross section is axis symmetrical, the equilibrium condition may be considered only in the circle of any given cross section. The equilibrium of the force in the circle with regard to a micro sector element having a circuitry thickness 1 which is cut with a center angle dθ and a coaxial cylinder of radius r and r+dr in any given cross section will be considered. Since the deformation is also axis symmetrical, shearing stress does not occur in ab surface and be surface, and therefore, only the vertical stress is exerted. For this reason, the equilibrium of the force in the circle can be expressed as shown in the following expression (5).

$$\sigma_r r d\theta + 2\sigma\theta_r \sin(d\theta/2) - (\sigma_r + (d\sigma_r/dr)dr)(r+dr)d\theta = 0 \quad (5)$$

In this case, dr is smaller than r, and $d\sigma_r$ is smaller than $\sigma_r$, and therefore, high order small terms included in the expression (5) are omitted, and when $\sin(d\theta/2) \approx d\theta/2$ is considered to hold, the expression (5) may be expressed as the expression (6) shown below.

$$rd\sigma_r/dr + \sigma_r - \sigma_\theta = 0 \quad (6)$$

Where the displacement in the circle of the radius r is u, the displacement in the same direction with u+dr is u+(du/dr)dr, and therefore, the distortion $\varepsilon_r$ in the circle of the radius r is $\varepsilon_r = du/dr$. With the displacement u of the circle, the circle of the radius r becomes the circle of the radius r+u. Therefore, the circumference distortion $\varepsilon_\theta$ can be expressed according to the following expression (7).

$$\varepsilon_\theta = (2\pi(r+u) - 2\pi r)/2\pi r = u/r \quad (7)$$

The following expression (8) or (9) can be obtained from the relational expression of the stress and the distortion.

$$d^2u/dr^2 + (1/r)(du/dr) - u/r^2 = 0 \quad (8)$$

$$d^2u/dr^2 + d(u/r)/dr = 0 \quad (9)$$

The following expression (10) can be obtained when the expression (8) or (9) is integrated.

$$u = c_1 r + c_2/r \quad (10)$$

Therefore, the following expressions (11), (12), and (13) are obtained.

$$\sigma_r = (E/((1+v)(1-2v)))(c_1 - (1-2v)(c_2/r^2) + v\varepsilon_z) \quad (11)$$

$$\sigma_\theta = (E/((1+v)(1-2v)))(c_1 + (1-2v)(c_2/r^2) + v\varepsilon_z) \quad (12)$$

$$\sigma_z = (Ev/((1+v)(1-2v)))(2c_1 + ((1-v)/v)\varepsilon_z) \quad (13)$$

Constant $c_1$, $c_2$ in the expressions (11), (12), (13) can be defined from peripheral condition, i.e., $\sigma_r = -p_a$ at the inner periphery $r=r_a$ of the cylinder and $\sigma_r = -p_b$ at the outer periphery $r=r_b$. The following expressions (14), (15), and (16) can be obtained from the expressions (11), (12), (13), respectively, from this peripheral condition. It should be noted that the displacement u can be expressed as the following expression (17).

$$\sigma_r = (1/(r_b^2 - r_a^2))(r_a^2(1 - r_b^2/r^2)p_a - r_b^2(1 - r_a^2/r^2)p_b) \quad (14)$$

$$\sigma_\theta = (1/(r_b^2 - r_a^2))(r_a^2(1 + r_b^2/r^2)p_a - r_b^2(1 + r_a^2/r^2)p_b) \quad (15)$$

$$\sigma_z = 2v(r_a^2 p_a - r_b^2 p_b)/(r_b^2 - r_a^2) + E\varepsilon_z = v(\sigma_r + \sigma_\theta) + E\varepsilon_z \quad (16)$$

$$u = ((1+v)(1-2v)/E)((r_a^2 p_a - r_b^2 p_b)/(r_b^2 - r_a^2))r + ((1+v)/E)((r_a^2 r_b^2)/((r_b^2 - r_a^2)r))(p_a - p_b) - v\varepsilon_z r \quad (17)$$

The expressions (16) and (17) include the term $\varepsilon_z$. Therefore, the expression (16) is different according to the constraint condition at the boundary of the cylinder of the target. For example, when both ends of the cylinder of the target are constrained, $\varepsilon_z = 0$ holds, and both ends are open, so that $\sigma_z = 0$ holds.

The shearing stress $\tau_r$ in the $r\theta$ plane can be expressed as shown in the following expression (18).

$$\tau_r = (\frac{1}{2})(\sigma_r - \sigma_\theta) = ((r_a^2 r_b^2)/((r_b^2 - r_a^2)r^2))p_b \quad (18)$$

The shearing stress $\tau_r'$ in the $\theta z$ plane is the maximum when $\sigma_z$ is 0, and therefore, where $\sigma_z = 0$ holds, this can be expressed as shown in the following expression (19).

$$\tau_r' = (\frac{1}{2})|\sigma_\theta| = (\frac{1}{2})((r_b^2)/(r_b^2 - r_a^2))(1 + r_a^2/r^2)p_b \quad (19)$$

Subsequently, the expression of Hagen-Poiseuille flow and modified Bernoulli will be explained.

When a fluid flows into the cylindrical tube, the pressure decreases as the fluid advances to the downstream, and the speed distribution of the flow also gradually changes. When the flow flows into the tube, the boundary layer develops from the tube wall, and as the flow advances to the downstream, the thickness of the boundary layer increases, and ultimately, the flow in the tube is covered with the boundary layer. For this reason, the speed distribution changes from a substantially flat distribution of the tube entrance into a downstream parabolic shape distribution, and thereafter, the speed distribution does not change. This state is referred to as a completely developed flow, and the pressure drop is also at a constant ratio with a tube frictional loss. A section where the flow reaches a developed flow from the tube entrance is referred to as an approach section or an entrance section, and the length of the section is referred to as an approach distance or an entrance length. The speed distribution of the completely developed flow does not change in the downstream direction, and therefore, as shown in the following expression (20), the action force of the pressure loss $\Delta P$ generated by the tube frictional loss and the frictional force of the shearing stress $\tau$ generated by the viscosity of the fluid are in equilibrium. In a case of a flow in a cylindrical tube, it is said to be a laminar flow when the Reynolds number Re is equal to or less than about 2300.

$$\tau = -\frac{r}{2}\frac{dp}{dx} = -\mu\frac{du}{dr} \quad (20)$$

In a case where the speed distribution u is a laminar flow, it is expressed as an axis symmetrical paraboloid of revolution as shown in the following expression (21).

$$u = \frac{R^2}{4\mu}\left(-\frac{dp}{dx}\right)\left\{1 - \left(\frac{r}{R}\right)^2\right\} \quad (21)$$

The amount of flow Q can be expressed as shown in the following expression (22) by integrating the speed distribution u over the entire tube cross section.

$$Q = \int_0^R u \cdot 2\pi r \, dr = \frac{\pi R^4}{8\mu}\left(-\frac{dp}{dx}\right) \quad (22)$$

The cross section average flow rate v can be expressed as shown in the following expression (23).

$$v = \frac{R^2}{8\mu}\left(-\frac{dp}{dx}\right) \quad (23)$$

The pressure inclination is constant in the flow direction, and the pressure decreases. The pressure inclination can be expressed as shown in the following expression (24) where the pressure drop $\Delta p$ of the tube length 1 is used. The expression (25) can be obtained by substituting the expression (22) into the expression (24). The expression (25) means that the amount of flow Q is proportional to the pressure loss Δp. The flow satisfying this relationship will be referred to as Hagen-Poiseuille flow.

$$-\frac{dp}{dx} = \frac{\Delta p}{1} \quad (24)$$

$$Q = \frac{\pi R^4}{8\mu} \frac{\Delta p}{1} \quad (25)$$

The expression of modified Bernoulli in a case where there is loss can be expressed as shown in the following expression (26).

$$\frac{p_1}{\rho g} + \frac{v_1^2}{2g} + z_1 = \frac{p_2}{\rho g} + z_2 + \Delta h \quad (26)$$

Δh denotes a loss head. The loss head is any one of a frictional loss head of the blood vessel wall, a loss head such as a stenosed portion (a loss head of a wide tube and a stenosis vessel), a branching portion, a bent tube circuitry, and the like, an entrance/exit loss head of an analysis target region entrance/exit circuitry of a blood vessel, and a loss head due to hydraulic ram caused by a change of pressure of an unsteady flow in a tube. For example, the tube frictional loss head is expressed by the following expression.

$$\Delta h = \frac{\Delta p}{\rho g} = \lambda \frac{1}{d} \frac{v^2}{2g} \quad (27)$$

In this case, l denotes the length of the tube, d denotes a tube internal diameter, v denotes an average speed of the tube, and λ denotes a tube frictional coefficient. In a case where the flow is a laminar flow, the tube frictional coefficient λ is a value determined by the Reynolds number Re, and in a case of a turbulent flow, the tube frictional coefficient λ is a value determined by the Reynolds number Re and the surface roughness. The frictional resistance is always exerted by the viscosity of the fluid. This frictional resistance consumes the energy or the motive power for driving the flow, and is therefore energy loss.

When Hagen-Poiseuille flow equation is determined like Darcy-Weisbach Equation, the following expression (28) of the pressure difference, the flow rate, and the tube internal diameter can be obtained.

$$\Delta p = \frac{64\mu}{vd} \frac{1}{d} \frac{v^2}{2} \quad (28)$$

Hagen-Poiseuille flow and modified Bernoulli expression have been hereinabove explained.

As described above, the image processing circuitry 27 can identify the latent variable by using the material dynamics expression and the Hagen-Poiseuille flow and modified Bernoulli expression. For example, a case where a tube diameter change is expressed by the internal pressure change and the elastic modulus using the material dynamics of the thick tube for the deformation of the blood vessel as the dynamical model will be considered. When the elastic modulus of the blood vessel wall and the plaque is set to a certain value in a case where the non-stress state is assumed to be an initial shape (for example, a state in which the blood vessel is most contracted), a relationship expression of the change amount of the internal pressure and the temporal change amount of the observation value of the blood vessel shape deformation index such as the average radius of the intravascular lumen can be obtained. The observation value of the blood vessel shape deformation index is measured from the time-series CT image. The temporal change of the internal pressure distribution of the blood vessel is determined so as to be in conformity with the temporal change amount of the observation value of the blood vessel shape deformation index. The prediction value of the blood vessel flow volume index is measured by performing the fluid analysis of the blood under the internal pressure distribution. In a case where the prediction value of the blood vessel flow volume index does not match the observation value, the image processing circuitry 27 changes the elastic modulus of the blood vessel wall or the plaque determined at first and further performs similar analysis. By repeating this, the image processing circuitry 27 can determine latent variables such as the pressure boundary condition of fluid analysis, the internal pressure distribution, and the elastic modulus of the blood vessel wall and the plaque in conformity with the observation value of the blood vessel shape deformation index and the observation value of the blood flow volume index. In order to perform this determination method in a more efficient and stable manner, statistical identification scheme based on hierarchical Bayesian model and Markov chain Monte Carlo method may be used.

As described above, the blood vessel analysis apparatus 50 according to the present embodiment includes the storage 33, the region setting circuitry 51, the image analysis/tracking processing circuitry 53, the dynamical model structuring circuitry 55, and the statistical identification circuitry 61. The storage 33 stores data of time-series medical images of blood vessels of a subject. The region setting circuitry 51 sets an analysis target region in a blood vessel region included in a time-series medical image. The image analysis/tracking processing circuitry 53 performs image processing on the time-series medical image to calculate the time-series morphology index and the time-series shape deformation index of the analysis target region. The dynamical model structuring circuitry 55 temporarily structures the dynamical model of the structural fluid analysis of the analysis target region based on the time-series morphology index, the time-series shape deformation index, and the time-series medical image. The statistical identification circuitry 61 identifies the latent variable of the dynamical model in the analysis target region so that the prediction values of the blood vessel morphology index and the blood flow volume index based on the dynamical model temporarily structured are in conformity with the observation values of the blood vessel morphology index and the blood flow volume index measured in advance.

According to the above configuration, the blood vessel analysis apparatus 50 according to the present embodiment can identify the latent variable such as material model, boundary condition, load condition, and geometric structure, and the like by performing inverse analysis using the blood vessel shape deformation index and the blood flow volume index. The blood vessel analysis apparatus 50 repeatedly performs the inverse analysis while changing the latent variable, so that the blood vessel analysis apparatus 50 can identify the latent variable in view of all of the four difficulties explained above, i.e., 1. the identification method of the material model of the coronary artery, 2. incorporation of the effect of the deformation of the shape of the heart to the coronary artery, 3. the identification method of the boundary condition of the coronary artery, and 4. the identification method of the load condition and the boundary condition and the material model using the blood vessel shape having uncertainty. Therefore, the blood vessel analysis apparatus 50 can execute the structural fluid analysis in view of the effect of the external factor such as the blood vessel, the heart, and the like that are not drawn in a CT image.

As described above, according to the present embodiment, the precision of the structural fluid analysis of the blood vessel can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A tubular structure analysis apparatus comprising:
a storage configured to store data of a plurality of images taken over time of a tubular structure of a subject;
a setting circuitry configured to set an analysis target region in a tubular structure region included in the plurality of images, and set an identification region for a latent variable in the analysis target region;
a calculation circuitry configured to calculate a time-series morphology index and a time-series shape deformation index of the analysis target region by performing image processing on the plurality of images;
a structuring circuitry configured to temporarily structure a dynamical model of a structural fluid analysis of the analysis target region, based on the time-series morphology index, the time-series shape deformation index, and the plurality of images;
an identification circuitry configured to estimate a prediction value of the time-series morphology index and a predicted flow volume index by performing stress analysis and fluid analysis on the structured dynamical model, and to identify the latent variable of the identification region so that the prediction value of the time-series morphology index and predicted flow volume index is in conformity with an observation value of the time-series morphology index calculated by the calculation circuitry and the predicted flow volume index;
an analysis circuitry configured to calculate a time-series dynamical index and/or a time-series fluid index by repeatedly performing perform stress analysis and/or fluid analysis on the dynamical model; and
an output circuitry configured to output the time-series dynamical index and/or the time-series fluid index,
wherein
the identification circuitry is configured to:
estimate the prediction value of the time-series morphology index by performing stress analysis on the temporarily structured dynamical model,
estimate the prediction value of the flow volume index by performing fluid analysis on the temporarily structured dynamical model,
set data distribution of errors between the prediction value of the time-series morphology index and the observation value and/or errors between the prediction value of the flow volume index and the observation value, allocate a prior distribution of errors to the latent variable of the temporarily structured dynamical model, calculate a posterior distribution based on the prior distribution and the data distribution, and identify the latent variable from a statistic value of the posterior distribution, and
wherein the output circuitry is configured to display a time-series dynamical model in animation with color values in accordance with the time-series dynamical index and/or the time-series fluid index.

2. The apparatus according to claim 1, wherein the identification circuitry identifies, as the latent variable, at least one of a material model of the identification region, a boundary condition of a flow inlet and outlet in the identification region, a load condition including an internal pressure distribution based on a stream in the identification region, and a geometric structure in the identification region.

3. The apparatus according to claim 2, wherein the identification circuitry includes:
a blood vessel stress analysis circuitry configured to estimate a prediction value of the morphology index by performing stress analysis on the temporarily structured dynamical model;
a blood fluid analysis circuitry configured to estimate a prediction value of the flow volume index by performing fluid analysis on the temporarily structured dynamical model;
a first statistical identification circuitry configured to statistically identify the latent variable so that the prediction value of the morphology index is in conformity with the observation value of the morphology index; and
a second statistical identification circuitry configured to statistically identify the latent variable so that the prediction value of the flow volume index is in conformity with the observation value of the flow volume index.

4. The apparatus according to claim 1, further comprising:
a control circuitry configured to control the structuring circuitry and the identification circuitry, and to store a predetermined identification termination index, and to repeat to estimate a prediction value of the time-series morphology index and a predicted flow volume index by performing stress analysis and fluid analysis on the structured dynamical model, while the latent variable is changed,
wherein the control circuitry determines whether the predetermined identification termination index attains an already-determined value every time the identification circuitry identifies the latent variable, and in a case where the identification termination index is determined not to have attained the already-determined value, the control circuitry controls the structuring circuitry to use the identified latent variable to restructure the dynamical model, and controls the identification circuitry to identify a latent variable of the restructured dynamical model, and in a case where the identification termination index is determined to have attained the already-determined value, the control circuitry controls the structuring circuitry to set a latest dynamical model as the ultimate dynamical model and to further output the latest dynamical model.

5. The apparatus according to claim 4, wherein:
the analysis circuitry is further configured to calculate a time-series mechanics index by performing stress analysis on the ultimate dynamical model; and the apparatus further comprise;
a display circuitry configured to display the time-series mechanics index.

6. The apparatus according to claim 4, further comprising:
the analysis circuitry configured to calculate a time-series fluid index by performing fluid analysis on the ultimate dynamical model; and
a display circuitry configured to display the time-series fluid index.

7. The apparatus according to claim 5, further comprising:
an amending circuitry configured to obtain the observation value of at least one of the time-series mechanics index and the flow volume index, and amend a shape of a blood vessel region included in the plurality of images so that a prediction value of at least one of a flow volume index and the time-series mechanics index based on the ultimate dynamical model is in conformity with the observation value of at least one of the time-series mechanics index and the flow volume index.

8. The apparatus according to claim 2, wherein the structuring circuitry structures a shape model of the analysis target region based on the time-series morphology index and the plurality of images, and allocates the time-series shape deformation index to the shape model as a forcible displacement, and structures the dynamical model by allocating the latent variable.

9. The apparatus according to claim 8, wherein the structuring circuitry classifies the dynamical model into a material model identification region and a non-identification region, and allocates a constraint condition of forcible displacement a surface portion of the material model identification region, and does not allocate the constraint condition of forcible displacement to an inside of the material model identification region, and allocates the constraint condition of forcible displacement to the surface portion and the inside of the non-identification region.

10. The apparatus according to claim 1, further comprising:
an association storage configured to receive and store a morphology index, a material model parameter, and a time-series space distribution of an internal pressure caused by a liquid pressure based on the dynamical model.

11. The apparatus according to claim 1, wherein the time-series morphology index and the time-series shape deformation index are given by probability distribution.

12. The apparatus according to claim 1, wherein
the tubular structure is a blood vessel of a subject,
the morphology index is a blood vessel morphology index relating to a morphological characteristic of a blood vessel region corresponding to the blood vessel,
the flow volume index is a blood flow volume index relating to a flow volume of a blood flowing in the blood vessel region, and
the structuring circuitry classifies the temporarily structured dynamical model into a plurality of partial regions according to a plaque index given by an ultrasonic diagnosis apparatus, and allocates a parameter for a material model to each of the plurality of partial regions.

13. The apparatus according to claim 1, wherein
the tubular structure is a blood vessel of a subject,
the morphology index is a blood vessel morphology index relating to a morphological characteristic of a blood vessel region corresponding to the blood vessel,
the flow volume index is a blood flow volume index relating to a flow volume of a blood flowing in the blood vessel region, and
the observation value of the blood flow volume index is a capacity of an intravascular lumen based on the time-series medical image, or an amount of blood flow.

14. A medical image diagnosis apparatus comprising:
an image-acquisition mechanism configured to generate data of a plurality of images taken over time of a tubular structure of a subject;
a setting circuitry configured to set an analysis target region in a tubular structure region included in the plurality of images, and set an identification region for a latent variable in the analysis target region;
a calculation circuitry configured to calculate a time-series morphology index and a time-series shape deformation index of the analysis target region by performing image processing on the time-series medical image;
a structuring circuitry configured to temporarily structure a dynamical model of a structural fluid analysis of the analysis target region, based on the time-series morphology index, the time-series shape deformation index, and the time-series medical image;
an identification circuitry configured to estimate a prediction value of the time-series morphology index and a predicted flow volume index by performing stress analysis and fluid analysis on the structured dynamical model, and to identify the latent variable of the identification region so that the prediction value of the time-series morphology index and predicted flow volume index is in conformity with an observation value of the time-series morphology index calculated by the calculation circuitry and the predicted flow volume index;
an analysis circuitry configured to calculate a time-series dynamical index and/or a time-series fluid index by repeatedly performing perform stress analysis and/or fluid analysis on an ultimate dynamical model while changing the identified latent variable for the identification region; and
an output circuitry configured to output the time-series dynamical index and/or the time-series fluid index, wherein
the identification circuitry is configured to:
estimate the prediction value of the time-series morphology index by performing stress analysis on the temporarily structured dynamical model,
estimate the prediction value of the flow volume index by performing fluid analysis on the temporarily structured dynamical model,
set data distribution of errors between the prediction value of the time-series morphology index and the observation value and/or errors between the prediction value of the flow volume index and the observation value, allocate a prior distribution of errors to the latent variable of the temporarily structured dynamical model, calculate a posterior distribution based on the prior distribution and the data distribution, and identify the latent variable from a statistic value of the posterior distribution;
wherein the output circuitry is configured to display a time-series dynamical model in animation with color values in accordance with the time-series dynamical index and/or the time-series fluid index.

15. A tubular structure analysis method comprising:

setting an analysis target region in a tubular structure region included in the plurality of images, and set an identification region for a latent variable in the analysis target region;

calculating a time-series morphology index and a time-series shape deformation index of the analysis target region by performing image processing on the plurality of images;

temporarily structuring a dynamical model of a structural fluid analysis of the analysis target region, based on the time-series morphology index, the time-series shape deformation index, and the plurality of images;

estimating a prediction value of the time-series morphology index and a predicted flow volume index by performing stress analysis and fluid analysis on the structured dynamical model, and identifying the latent variable of the identification region so that the prediction value of the time-series morphology index and predicted flow volume index is in conformity with an observation value of the time-series morphology index calculated by the calculating and the predicted flow volume index;

calculating a time-series dynamical index and/or a time-series fluid index by repeatedly performing stress analysis and/or fluid analysis on an ultimate dynamical model; and outputting the time-series dynamical index and/or the time-series fluid index, wherein further comprising:

estimating the prediction value of the time-series morphology index by performing stress analysis on the temporarily structured dynamical model, estimating the prediction value of the flow volume index by performing fluid analysis on the temporarily structured dynamical model, setting data distribution of errors between the prediction value of the time-series morphology index and the observation value and/or errors between the prediction value of the flow volume index and the observation value, allocating a prior distribution of errors to the latent variable of the temporarily structured dynamical model, calculating a posterior distribution based on the prior distribution and the data distribution, and identifying the latent variable from a statistic value of the posterior distribution;

wherein the outputting displays a time-series dynamical model in animation with color values in accordance with the time-series dynamical index and; or the time-series fluid index.

* * * * *